United States Patent
Garrett

(10) Patent No.: US 10,912,752 B2
(45) Date of Patent: *Feb. 9, 2021

(54) METHODS AND COMPOSITIONS FOR REDUCING OCULAR DISCOMFORT

(71) Applicant: Brien Holden Vision Institute Limited, Sydney (AU)

(72) Inventor: Qian Garrett, Barden Ridge (AU)

(73) Assignee: Brien Holden Vision Institute Limited, Sydney (AU)

(*) Notice: Subject to any disclaimer, the term of this patent is extended or adjusted under 35 U.S.C. 154(b) by 0 days.

This patent is subject to a terminal disclaimer.

(21) Appl. No.: 16/114,902

(22) Filed: Aug. 28, 2018

(65) Prior Publication Data

US 2019/0167625 A1 Jun. 6, 2019

Related U.S. Application Data

(63) Continuation of application No. 14/389,143, filed as application No. PCT/AU2013/000327 on Mar. 28, 2013, now Pat. No. 10,085,960.

(30) Foreign Application Priority Data

Mar. 30, 2012 (AU) ................................ 2012901278

(51) Int. Cl.
A61K 31/205 (2006.01)
A61K 9/00 (2006.01)
G02C 7/04 (2006.01)

(52) U.S. Cl.
CPC .......... *A61K 31/205* (2013.01); *A61K 9/0048* (2013.01); *G02C 7/04* (2013.01)

(58) Field of Classification Search
CPC .......... A61K 31/205; A61K 9/00; G02C 7/04
See application file for complete search history.

(56) References Cited

U.S. PATENT DOCUMENTS

2006/0067981 A1 3/2006 Xa
2006/0106104 A1 5/2006 Vehige et al.
2010/0330146 A1 12/2010 Chauhan et al.

FOREIGN PATENT DOCUMENTS

| TW | 200631605 | 9/2006 |
| WO | WO 2007/003481 | 1/2007 |
| WO | WO 2008/071528 | 6/2008 |
| WO | WO 2009/094466 | 7/2009 |
| WO | WO 2010/047927 | 4/2010 |
| WO | WO 2010/141648 | 12/2010 |

OTHER PUBLICATIONS

Preliminary Report on Patentability dated Oct. 1, 2014 for PCT/AU2013/000327.
International Search Report dated May 6, 2013 for PCT/AU2013/000327.
Flanagan, J. L. et al., "Role of Carnitine in Disease", Nutrition & Metabolism, 2010, 7:30.
Corrales, R. M., et al., "Effects of Osmoprotectants on Hyperosmolar Stress in Cultured Human Corneal Epithelial Cells", Cornea, 2008, Vo. 27., No. 5, pp. 574-579.
PubChem information sheet for betaine.
University of Maryland Medical Center, 1997.

*Primary Examiner* — Zohreh A Fay
(74) *Attorney, Agent, or Firm* — Jones Day

(57) ABSTRACT

The invention relates to compositions and devices which include an osmolytic agent, in particular a betaine or carnitine compound, for reducing ocular discomfort associated with various diseases or conditions, in particular diseases or conditions associated with high tear film tonicity. The invention also relates to methods of treating or preventing various diseases or conditions using compositions and devices of the invention.

20 Claims, 17 Drawing Sheets

Specification includes a Sequence Listing.

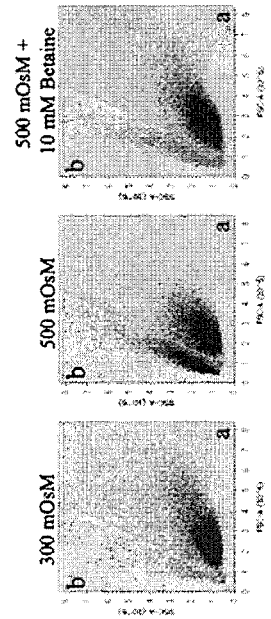
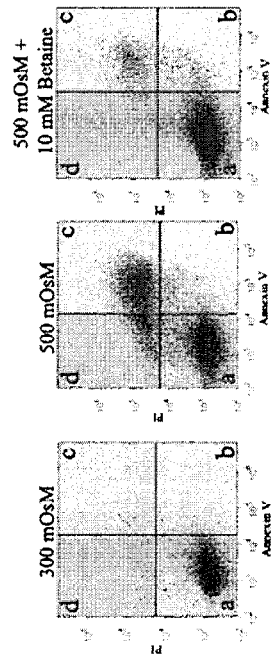
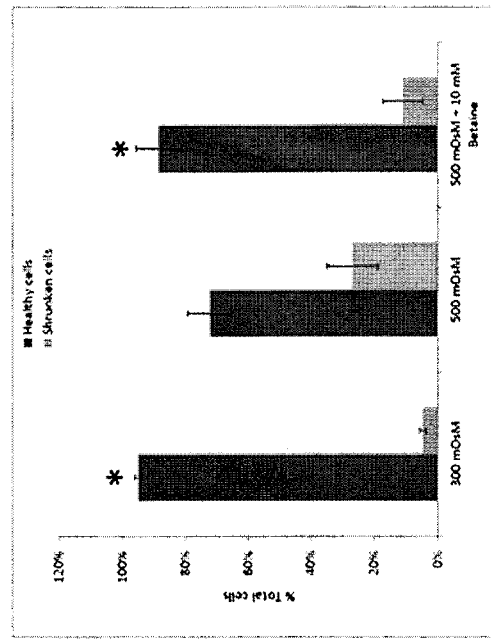
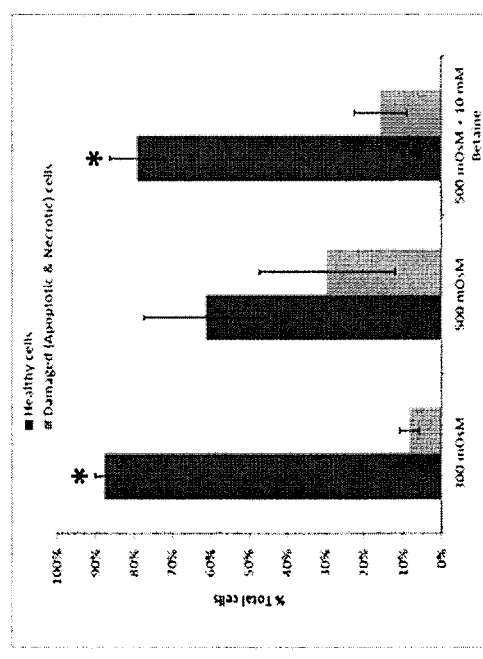
FIGURE 2A
FIGURE 2B

FIGURE 6A
FIGURE 6F
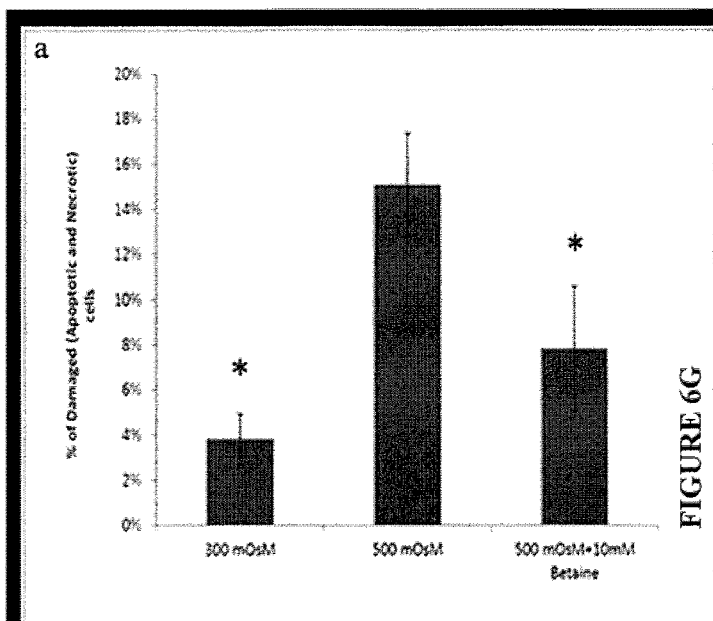
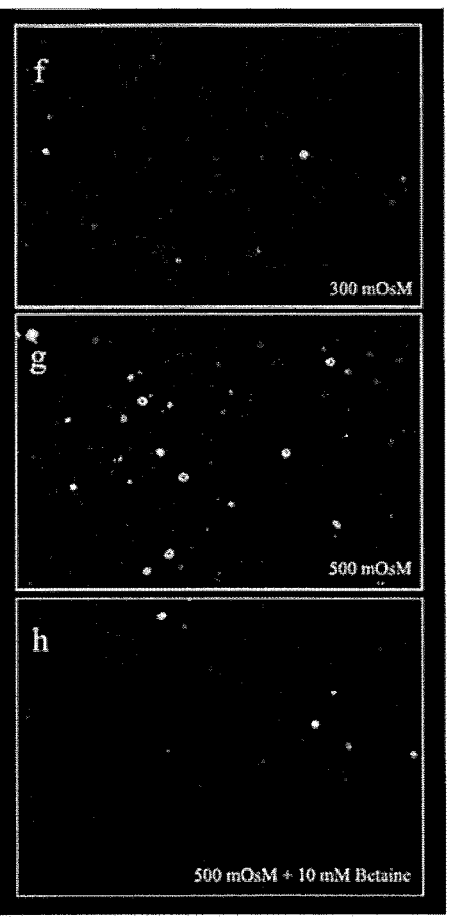
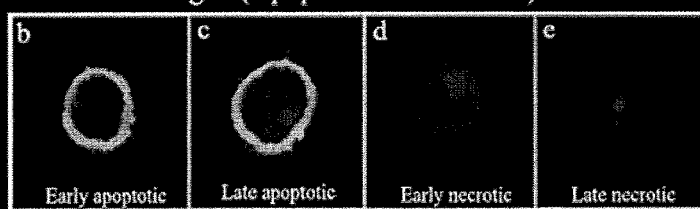
FIGURE 6B   FIGURE 6C   FIGURE 6D   FIGURE 6E
FIGURE 6H A) Cell size analysis B) Annexin V and PI Staining

AA

AB

AC

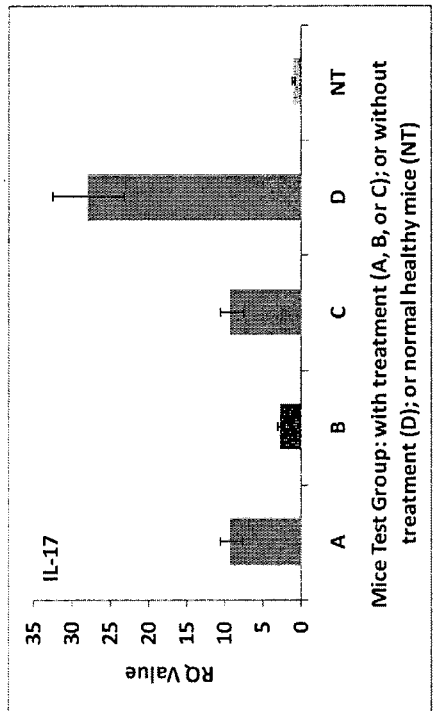
FIGURE 16A
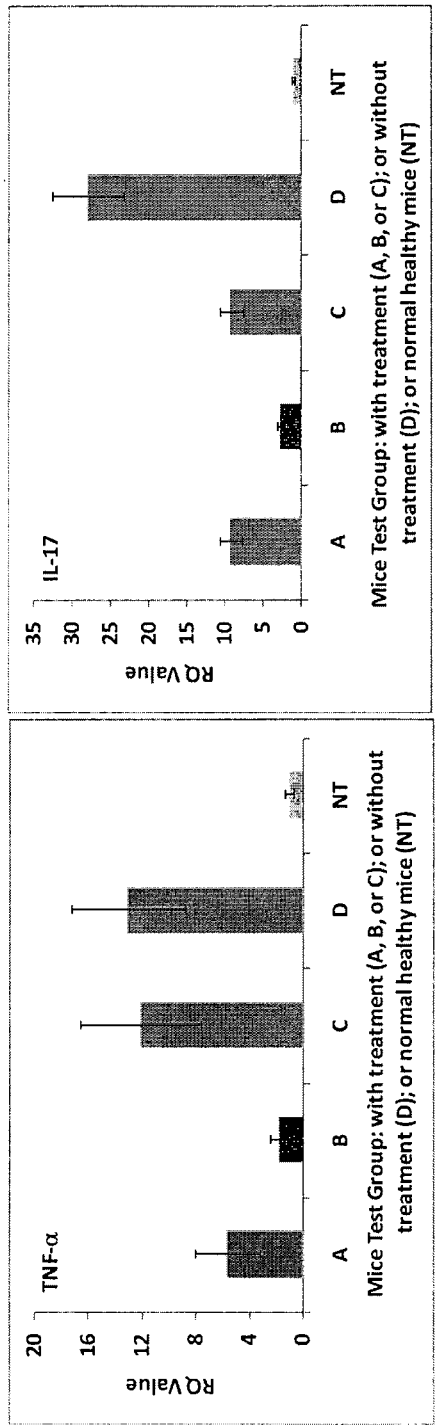
FIGURE 16B
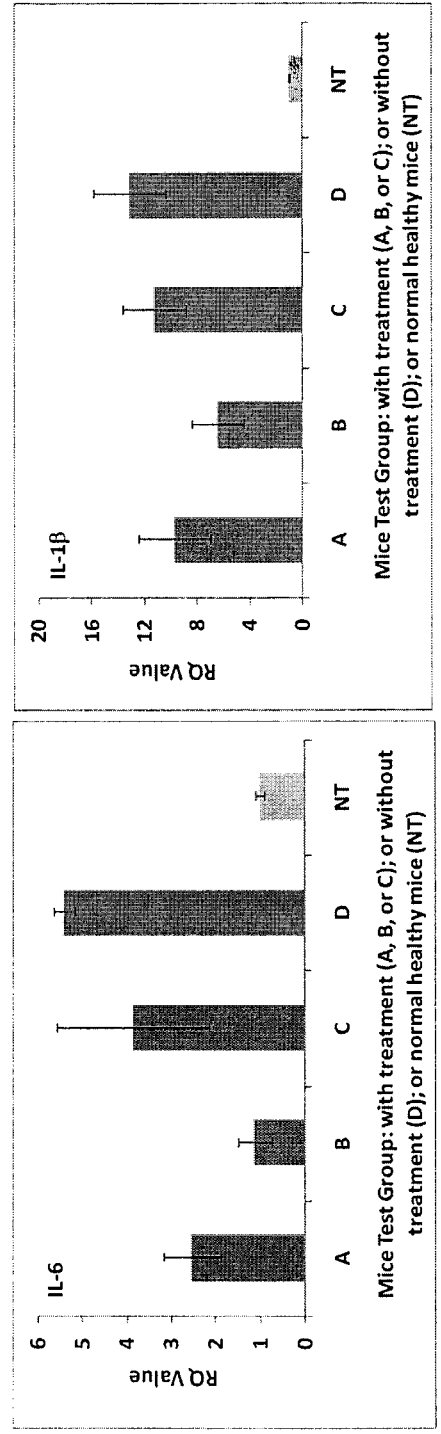
FIGURE 16C
FIGURE 16D

METHODS AND COMPOSITIONS FOR REDUCING OCULAR DISCOMFORT

CROSS-REFERENCE TO RELATED APPLICATION

This application is a continuation of U.S. application Ser. No. 14/389,143, filed 29 Sep. 2014, which is the National Phase Application of International Application No. PCT/AU2013/000327, filed 28 Mar. 2013, which designates the United States and was published in English, and claims priority to Australian Patent Application No. 2012901278 dated 30 Mar. 2012. These applications, in their entirety, are incorporated herein by reference.

SEQUENCE LISTING

The instant application contains a Sequence Listing which has been filed electronically in ASCII format and is hereby incorporated by reference in its entirety. Said ASCII copy, created on Feb. 4, 2019, is named 0135740077999_SL.txt and is 2,631 bytes in size.

FIELD OF THE INVENTION

The invention relates to compositions and devices which include an osmolytic agent, in particular a betaine or carnitine compound, for reducing ocular discomfort associated with various diseases or conditions, in particular diseases or conditions associated with high tear film tonicity. The invention also relates to methods of treating or preventing various diseases or conditions using compositions and devices of the invention.

BACKGROUND OF THE INVENTION

Dry eye is a common disease of the ocular surface affecting millions and is characterized by dryness, irritation, blurred vision and tear instability. One of the key pathological factors of dry eye is an increase in tear osmolarity. Tear film tonicity of dry eye patients generally ranges between 320 and 400 mOsm, and increased tonicity of the tear film has also been reported to be correlated with severity of dry eye disease. Tear film hyperosmolarity causes ocular discomfort and inflammation. Hyperosmolar stress stimulates the production of interleukin-1 (IL-1), IL-6, IL-8 and tumor necrosis factor-α (TNF-α), and proteolytic enzymes such as MMP-9 from corneal epithelial cells.

Hypertonicity causes deleterious altered functioning of the cells, and the immediate effect of hypertonicity is decreased cell volume (cell shrinkage) which is counteracted by accumulation of intracellular components, including inorganic ions and macromolecules, resulting in an immediate and efficient regulation of cell volume. However, this accumulation of inorganic ions can disrupt protein stability and lead to cell death by apoptosis. Hypertonicity-induced apoptosis in human corneal epithelial cells occurs via a cytochrome c-mediated apoptotic pathway which is affected by the JNK and ERK/MAPK signalling pathways. MAP kinases regulate gene transcription by activating transcription factors for cytokines including TNF-α. TNF-α in turn mediates apoptosis by activating caspase-8 through the extrinsic apoptotic pathway and through inflammation. Additionally, increased production of TNF-α by human limbal epithelial cells has been correlated with increasing medium osmolarity.

A significant obstacle to contact lens wear for many people is comfort. Putting aside people who have pre-existing eye conditions that reduce the comfort of contact lens wear, the wearing of contact lenses can cause discomfort in otherwise healthy eyes.

Contact lenses in use today fall into two general categories. Hard type lenses are formed from materials prepared by the polymerization of acrylic esters, such as poly(methyl methacrylate) (PMMA). Gel, hydrogel or soft type lenses are made by polymerizing such monomers as 2-hydroxyethyl methacrylate (HEMA) or, in the case of extended wear lenses, made by polymerizing silicon-containing monomers or macromonomers. An example of a soft type contact lens is a silicone hydrogel lens.

Moreover, in people who have a disorder resulting in an excessively curved cornea or protrusion of the cornea, wearing a contact lens can be an important part of treatment. This is not feasible however if it causes significant discomfort. Also, children are more likely to object to contact lens wear if it is uncomfortable, although it may be preferable for at least some children to wear contact lenses rather than glasses or no eye-correction at all.

It has been reported that discontinuations of contact lens wear can be as high as 50%. Studies have found that the main reason of contact lens drop outs is due to symptoms of ocular discomfort during contact lens wear. It is well known that contact lens drop out is one of the main causes for the global contact lens market being unable to grow. Contact lens wear can cause disruption to the tear film leading to dry eyes. This dry eye can increase the tonicity of the tear film leading to discomfort for the contact lens wearer. Soft contact lenses and extended wear lenses typically contain water, usually 24 to 75% or higher. Evaporation of water from within the contact lens causes the contact lens to replenish this water by absorption of water from the tear layer of the eye. If the tear layer is dehydrated the contact lens becomes uncomfortable and vision is compromised.

There exists a need for compositions and methods for ameliorating the discomfort associated with increased tear film tonicity associated with various diseases and conditions, in particular in contact lens wearers.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

The present invention addresses one or more of the problems with the prior art outlined above.

In one aspect, the present invention provides an ophthalmic device including a physiologically acceptable osmolytic agent such as betaine or carnitine, wherein the device permits a therapeutically effective amount of the agent to be desorbed from the device into the eye during wear. Typically the device permits an agent to be desorbed by being able to releasable absorb an osmolytic agent. In a preferred embodiment, the osmolytic agent is a betaine compound or a carnitine compound or a combination of both, preferably trimethylglycine and/or L-carnitine. The betaine compound may also be proline betaine. Typically, the device includes one or more betaine compounds and/or one or more carnitine compounds.

In one embodiment, the device is a contact lens, preferably a single use contact lens. The single use contact lens may be for either daily or extended wear. Preferably, the contact lens is a silicone hydrogel lens.

In another embodiment, the device permits the osmolytic agent to be desorbed over about a 2, 4, 6, 8, 10, 12 or 24 hour period.

In any aspect of the invention, the ophthalmic device is capable of inhibiting, ameliorating or reducing ocular discomfort associated with high tear film tonicity. Without being bound by any theory or mode of action, release of an osmolytic agent from a device, such as a contact lens, in situ into the tear film allows the agent to be taken up by cells in the eye, including corneal epithelial cells, which increases the intracellular osmolarity and in turn reduces the osmotic pressure that cells experience as a result of high tear film tonicity. This reduction in osmotic pressure that the cells experience reduces the likelihood that a cell will reduce in volume, undergo apoptosis and generate ocular discomfort.

In a further aspect, an ophthalmic device of the invention further includes a diffusion attenuator. Preferably, the diffusion attenuator is vitamin E as explained below. The diffusion attenuator can be any combination of a liquid that modifies the molecular diffusivity of the device or a plurality of phase separated liquid aggregates or solid particles dispersed to act as barriers to the diffusion of one or more osmolytic agents included within the device. Where vitamin E is present in an ophthalmic device of the invention, preferably the vitamin E is present in or on the device prior to the addition of the betaine or carnitine compound.

Preferably, the ophthalmic device includes the osmolytic agent, such as a betaine compound and/or carnitine compound, in any way such that the agent is capable of being desorbed from the device and is then available for entry into ocular cells such as corneal epithelial cells. The ophthalmic device may include agent in any way such that the agent is available to reduce the osmotic pressure in corneal epithelial cells which arises from an abnormally high tonicity in the extracellular environment. Preferably, the agent is a betaine compound and/or a carnitine compound. Preferably, the betaine compound and/or carnitine compound is presented at the interface between the device and the cornea.

In one embodiment, the betaine compound and/or carnitine compound is integral with the ophthalmic device, for example, the betaine compound and/or carnitine compound is added to the device during manufacture. In this embodiment, the betaine compound and/or carnitine compound is present within the device. In another embodiment, the betaine compound and/or carnitine compound may also be added to the exterior of the ophthalmic device any time after manufacture wherein an effective amount of compound is capable of being desorbed from the device. Preferably, the device is packaged in a solution that contains one or more osmolytic agents.

In a preferred embodiment, the structural composition or polymer of an ophthalmic device, such as a contact lens, referred to herein does not include a betaine compound. In other words, the structural composition or polymer of an ophthalmic device is betaine free.

Preferably, the amount of osmolytic agent such as a betaine compound and/or a carnitine compound included in the device is sufficient to reduce the osmotic pressure in the corneal epithelial cells for the duration of application of the device to the eye. Even more preferably, the amount of betaine compound and/or carnitine compound included in the device is sufficient to inhibit, ameliorate or reduce corneal epithelial cells from shrinking.

A device of the invention is particularly suitable for use in subjects with an abnormally high tear film tonicity. Those subjects may have a tear film tonicity greater than about 300, 400, 500, 600 or 700 mOsm. Typically, a subject with abnormally high tear film tonicity has a tonicity in the range between about 300 mOsm to about 500 mOsm, even more typically range is between 320 to 400 mOsm. Typically those subjects are clinically diagnosed as having Dry Eye Syndrome (DES).

In another aspect, the present invention provides use of an ophthalmic device including a physiologically acceptable osmolytic agent such as betaine or carnitine, for the treatment, prevention or inhibition of ocular discomfort, wherein the device permits a therapeutically effective amount of the agent to be desorbed from the device into the eye during wear.

Preferably, the use of an ophthalmic device of the invention is for the treatment, prevention or inhibition of ocular discomfort that is associated with Dry Eye Syndrome or contact lens wear.

In a further aspect there is provided a method of inhibiting, reducing or ameliorating ocular discomfort associated with high tear film tonicity in a subject including the step of
  applying an ophthalmic device of the invention to a subject identified as having or being at risk of developing tear film with high tonicity,
thereby inhibiting, reducing or ameliorating ocular discomfort associated with high tear film tonicity in a subject.

In a further aspect there is provided a method of inhibiting, reducing or ameliorating ocular discomfort associated with high tear film tonicity in a subject including the steps of
  determining whether a subject has or is at risk of developing tear film with high tonicity; and
  applying an ophthalmic device of the invention to a subject identified as having or being at risk of developing tear film with high tonicity,
thereby inhibiting, reducing or ameliorating ocular discomfort associated with high tear film tonicity in a subject.

In another aspect, the present invention provides a method for inhibiting, reducing or ameliorating ocular discomfort associated with high tear film tonicity in a subject including applying an ophthalmic device of the invention to a subject.

In a preferred embodiment, the present invention provides a method for inhibiting, reducing or ameliorating ocular discomfort associated with high tear film tonicity in a subject identified as having Dry Eye Syndrome or high tear film tonicity including applying an ophthalmic device of the invention to the subject.

In a further aspect, the present invention provides use of a betaine and/or a carnitine compound in the preparation of a medicament for inhibiting, reducing or ameliorating ocular discomfort associated with high tear film tonicity. Preferably, the medicament is an ophthalmic device, even more preferably a contact lens. Where the medicament is an ophthalmic device, the medicament permits a therapeutically effective amount of the agent to be desorbed from the device into the eye during wear In another embodiment there is provided a kit for use in a method of the invention mentioned above, the kit including:
  a container holding an ophthalmic device, or composition of the invention; and
  a label or package insert with instructions for use.

In a further embodiment there is provided a kit when used in a method of the invention mentioned above.

In another embodiment there is provided a kit for use in a method of the invention mentioned above, the kit including:

an ophthalmic device of the invention; and a label or package insert with instructions for use.

In a further embodiment there is provided a kit when used in a method of the invention mentioned above.

In certain embodiments the kit may contain one or more further ingredients for preventing discomfort, improving comfort or ameliorating decrease in ocular comfort during wearing of a contact lens/ophthalmic device.

In another aspect, the present invention also relates to a method of making an ophthalmic device for inhibiting, reducing or ameliorating ocular discomfort associated with high tear film tonicity including an effective amount of an osmolytic agent, such as a betaine and/or carnitine compound, including the step of contacting an ophthalmic device with a solution comprising the agent during manufacture such that the agent is capable of being desorbed from the device during wear.

Alternatively, the present invention provides a method for producing an ophthalmic device with an osmolytic agent including the step of contacting the device with a composition including the osmolytic agent, such as a betaine and/or carnitine compound, for a time sufficient for the agent to be absorbed into the matrix of the device. The level of absorption is such that the agent is capable of being desorbed from the device when in use for a period of day wear. Preferably, the device is a contact lens, even more preferably the contact lens is single use. An osmolytic agent may be contacted with the ophthalmic device prior to selling or delivering the ophthalmic device to a subject (e.g. adding a betaine and/or carnitine compound to a solution prior to sealing the package, and subsequently sterilizing the package) or during the preparation of the ophthalmic device.

In one embodiment the ophthalmic device is a contact lens. Preferably, the contact lens is a soft contact lens. An example of a soft type contact lens is a silicone hydrogel lens. The lens may be prepared by soaking the lens in a solution containing a solution including a betaine and/or carnitine compound. Typically, the lens is soaked in the solution for 15 mins to 8 hours, preferably for 1 hour. The betaine and/or carnitine compound is desirably present in the solution in an amount ranging from 0.01 to 10% weight by volume. In one embodiment, it is present in an amount ranging from 0.1 to 5% weight by volume. In one embodiment, the betaine and/or carnitine compound is essentially the only active ingredient of the solution In a preferred embodiment, an ophthalmic device of the invention is prepared by absorption of the osmolytic agent from a solution of between 5 to 20 mM. Preferably, the osmolytic agent is a betaine and/or carnitine compound. For example a betaine compound may be present in an ophthalmic device, for example a contact lens, in a range of about 1.0 µg to 15 µg, preferably 1.2 µg to 12 µg and/or a carnitine compound may be present in the range of about 1.0 µg to 20 µg, preferably 1.6 µg to 16 µg. Further, a betaine compound may be present in the lens in a range of about 0.05% to 0.2% w/w and/or a carnitine compound may be present in the range of about 0.08% to 0.3% w/w. Preferably, any amount of a betaine and/or a carnitine compound is present in the lens such that when used in a method as described herein a tear film concentration of about 5 to 100 mM of desorbed compound, preferably about 5 to 50 mM, even more preferably about 20 mM, is provided.

In a further aspect, the present invention provides a method of inhibiting, reducing or ameliorating ocular discomfort in a subject including administering a betaine compound to the eye, wherein the subject has been diagnosed with a condition that is associated with high tear film tonicity. Preferably, the condition is Dry Eye Syndrome. In one embodiment, betaine is administered to the eye in the form of eye drops. In another embodiment, betaine is administered to the eye by being desorbed from an ophthalmic device. Preferably, betaine is the only pharmaceutically active component in the eye drop.

In another aspect, the present invention provides a composition including a betaine and/or carnitine compound as the only pharmaceutically active component. Preferably, the composition further includes a physiologically acceptable carrier, diluent or excipient. The present invention does not include the compositions described in PCT/US2005/041064 or US 2010/0184664. In preferred embodiments, a composition of the present invention does not include erythritol or is erythritol-free.

Any composition of the invention may be provided in a kit, pack or container for use by a subject to increase the amount of osmolytic agent, preferably a betaine or carnitine compound, to be desorbed from an ophthalmic device, preferably a contact lens. For example, a kit, pack or container containing the composition may be used by a subject to contact the ophthalmic device for a sufficient time for the agent to be absorbed into the matrix of the device. The kit, pack or bottle may include instructions directing the subject to contact the ophthalmic device with the composition of the invention. The ophthalmic device, preferably contact lens, may be for extended wear or are reusable and the instructions may direct the subject to contact the device with the composition.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIGS. 2A and 2B. Flow cytometry analysis of the effect of hyperosmolarity on cellular apoptosis (A) and cell volume (B):

FIG. 2A (I) are representative dot plots showing the flow cytometry analysis performed using Annexin V (indicating apoptosis) and PI (necrosis) for cell viability. The population of healthy cells are shown in the lower left corner 'a' of the dot plots. These are the ones that stain negative for both Annexin V and PI. The population of cells represented by the quandrant 'b' (lower right quadrant) stained negatively for PI but positive for Annexin V binding, indicating the population of early apoptotic cells. Quandrant 'c' positively stained for both Annexin V and PI, indicating loss of membrane integrity. Hence this quadrant represents the late apoptotic cells. Finally, the quadrant 'd' depicts cells negative for Annexin V binding, but positive for PI indicating complete loss of cell membrane and thus representing necrotic cells. FIG. 2A (II) shows the statistical analysis of the healthy cells (under isotonic condition, 300 mOsM) and apoptotic cells under 500 mOsm with or without betaine (10 mM). * Represents significant difference (p<0.05) observed in the percentage of healthy cells under isotonic condition (300 mOsm) compared to cells under hyperosmotic stress (500 mOsm). On treatment with 10 mM Betaine under hypertonic conditions (500 mOsm+10 mM betaine), considerable increase in the percentage of healthy cells was observed, similar to those in the isotonic conditions. FIG. 2B (I) depicts representative images of the flow cytometry analysis of the effect hyperosmolar shock on the cell volume with and without betaine (10 mM). Here, the right polygon 'a' indicates the population of healthy cells. As against this, the polygon 'b' represents the population of shrunken cells. FIG. 2B (II) shows statistical analysis of the percentage of healthy and shrunken cells. Significant reduction (p<0.05) in the percentage of healthy cells was observed on subjecting to hyperosmolar shock. The percentage of healthy cells significantly increased on administration of 10 mM Betaine to 500 mOsm, approaching to that of cells under isotonic conditions (300 mOsM).

FIGS. 6A, 6B, 6C, 6D, 6E, 6F, 6G, and 6H. Annexin V/PI staining of HCLE a) Statistical analysis of percentage of damaged cells when subjected to hyperosmolar conditions compared to isotonic conditions, and the osmoprotective effect of betaine. * shows statistical significant difference (p>0.05) compared to when the cells are subjected to hyperosmotic conditions. The damaged cells comprise early apoptotic cells (b), late apoptotic cells (c), early necrotic (d) and late necrotic (e), Images were obtained at 60× using confocal microscope. The figures (f)(g)(h) are representative images of the cells in 300 mOsM, 500 mOsM and 500 mOsM+10 mM betaine respectively and were obtained at 10× with confocal microscope.

FIG. 7A (1) represent flow cytometry dot plots showing the population of healthy and shrunken cells in response to hyperosmolarity treatments with or without carnitine (10 mM). It is seen that the number of damaged/shrunken cells (represented by polygon 'b') increased greatly; consequently decreasing the healthy cell population represented by polygon 'a' when subjected to hyperosmotic conditions. FIG. 7A (II) shows statistical analysis of percentages of healthy and shrunken cells obtained from the flow cytometry data. The number of shrunken cells reduced visibly when cells are exposed to 500 mOsm in the presence of carnitine. FIG. 7 B(I) and FIG. 7B (II) respectively show the apoptotic cells and representative images of flow cytometry analysis and statistical analysis of the percentages of healthy cells. From the flow cytometry analysis it is evident that the percentage of apoptotic and necrotic cells (represented by quadrant b, c, d in FIG. 7B (II)) is comparatively high in cell subjected to hyperosmotic stress and which reduced when administered with 10 mM of osmoprotectant carnitine. Consequently, the population of healthy cells (represented by quadrant 'a' in FIG. 7B (II)), increased on treatment with 10 mM Carnitine.

FIGS. 16A, 16B, 16C, and 16D. mRNA expression of TNF-α, IL-17, IL-6 or IL-1β of mice conjunctivas by qRT-PCR after mice were housed in ICSE for 21 days without any treatment followed by continued housing and topical treatment with A, B, or C at four times a day (starting at Day 22), or without treatment (D) for a further 14 days. Normal healthy mice without housing or the treatments were used as normal healthy control.

DETAILED DESCRIPTION OF THE EMBODIMENTS

Figure 1:
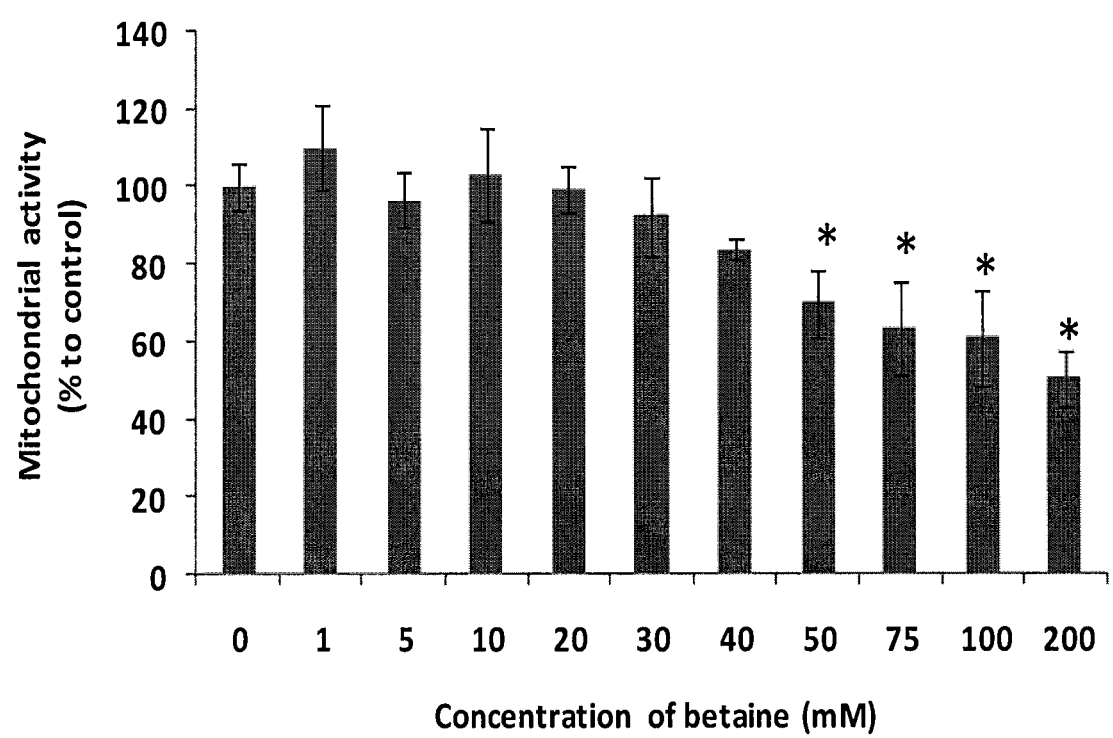
FIG. 1. HOLE cell mitochondrial activity after exposure for 16 h to betaine (1.0-200 mM in culture medium with osmolarity of 300 mOsm). * represents significant difference of the betaine treated groups compared to the control without betaine ($p<0.05$, $n=6$).

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

The present invention is based on the release of an osmolytic agent, such as a betaine and/or a carnitine compound, from an ophthalmic device in situ to alleviate ocular discomfort resulting from high tear film tonicity. Without being bound by any theory or mode of action, release of these agents from a contact lens in situ into the tear film allows the agents to be taken up by cells in the eye, including corneal epithelial cells, which in turn increases the intracellular osmolarity and reduces the osmotic pressure that cells experience as a result of high tear film tonicity. This reduction in osmotic pressure that the cells experience reduces the likelihood that a cell will undergo apoptosis and generate discomfort.

It has been found that betaine and/or carnitine compounds are useful in treating the discomfort associated with eye conditions and disorders such as Dry Eye Syndrome (DES). DES (sometimes also referred to as "dry eye disorder") is a disorder of the normal tear film that results from one of the following:
  decreased tear production;
  excessive tear evaporation;
  an abnormality in the production of mucus or lipids normally found in the tear layer.

Aqueous (watery) tear deficiency is caused by either poor production of watery tears or excessive evaporation of the watery tear layer. Poor production of tears by the tear glands may be a result of age, hormonal changes, or various autoimmune diseases, such as primary Sjogren syndrome, rheumatoid arthritis, or lupus. Evaporative loss of the watery tear layer is usually a result of an insufficient overlying lipid layer (which may be caused by, for example, a deficiency in oil production from the meibomian glands). In addition, some medications, such as antihistamines, antidepressants, beta-blockers, and oral contraceptives, may decrease tear production.

An advantage of the present invention includes an effective means to reduce ocular discomfort during contact lens use. The present invention may provide this reduction in ocular discomfort for the duration of contact lens wear. Providing a betaine and/or carnitine compound via an ophthalmic device in situ alleviates the need for application of an additional formulation, such as an eye drop or an artificial tear.

Embodiments of the invention include the use of a diffusion attenuator such as vitamin E. This form of the invention is advantageous as the slow release of an osmolytic agent, such as a betaine and/or carnitine compound, allows a more prolonged reduction in ocular discomfort for subjects who require prolonged use of contact lens. Therefore, the reduction in ocular discomfort may be concomitant with the duration of contact lens use. In addition, the slow or attenuated release of a betaine and/or carnitine compound is particularly useful in repeated use contact lenses and alleviates the need for repeated application of the compound to the device. For a single use contact lens the agent diffuses over enough of the day, e.g. 6, 8, 10 or 12 hours, such that discomfort is ameliorated or avoided.

Other means for attenuating diffusion of the osmolytic agent include using ligand-containing ophthalmic devices, such as contact lenses, as a vehicle for delivering compounds. This strategy is based on weak interactions between compounds and ligands in polymer matrix including hydrogen bonds, electrostatic interactions, and host-guest interactions which can induce the compound loading and control its release. Cationic or anionic ion ligand functional groups incorporated in lens polymer matrix would be useful and the release of the osmolytic agent is likely to be through ion exchange. Such methods are described more fully in Hu et al. *International Journal of Polymer Science*. Volume 2011 (2011), Article ID 814163, 9 pages.

Another means for attenuating diffusion includes preparing an ophthalmic device with a controlled hydrophilic/hydrophobic copolymer ratio. Incorporation of hydrophilic monomers in a contact lens polymer will increase the interaction between hydrophilic compounds and the polymer matrix, especially in silicon hydrogel lenses which contain hydrophobic silicones. The ratio of hydrophilic/hydrophobic copolymer is material dependent and should balance the need for other lens properties such as optimal lens mechanical properties, water content, ion permeability and transparency. Such methods are described more fully in Hu et al. above.

A further method of attenuating diffusion is ophthalmic device with inclusion of compounds in a colloidal structure dispersed in the device using nanoparticles, nanoemulsions, nanosuspensions, and liposomes. Nanoparticles vary in size from 10 to 1000 nm and in the application of contact lenses are preferably in a size of less than 50 nm. A carnitine or a betaine compound may be dissolved or dispersed into the polymer solution and emulsified into an aqueous solution to make a water in oil microemulsion. Compound loading in the nanoparticles can be achieved either by incorporating the drug at the time of nanoparticle production or by adsorbing the drug after the formation of nanoparticles by incubating the nanoparticles in a solution containing the compound Such methods are described more fully in: Diebold and Calonge et al. *Progress in Retinal and Eye Research*, (2010), 29: 596-609, Kumar et al. *Journal of Advanced Pharmaceutical Technology & Research*, (2013) 4(1): 9-17, Gulsen and Chauhan, *Investigative Ophthalmology & Visual Science*, (2004), 45(7): 2342-2347, Gulsen and Chauhan, *International Journal of Pharmaceutics* (2005), 292: 95-117).

Another means of attenuating diffusion is molecularly imprinted polymeric hydrogels. Such methods are described more fully in Singh et al. *Journal of Basic and Clinical Pharmacy*, (2001), 002 (002): 87-101, may be applicable. Imprinting forms a memory pocket for a template molecule, for example a carnitine compound or a betaine compound, embedded within a polymer network during lens polymer synthesis. Affinity can be tailored by varying the number and strength of interactions between the carnitine and/or betaine compounds and lens polymer, and their release can be influenced by polymer mesh size, template size and the interaction of the carnitine and/or betaine compounds with the polymer chain.

An "osmolytic agent" or "osmolyte" is a compound that substantively affects osmosis. This is readily assessed empirically in a given environment. In particular, an osmolytic agent or osmolyte acts to balance osmotic pressure and preferably does not participate in cell metabolism. These compounds have osmoprotectant properties when capable of moving across a barrier between fluids of different osmolarity, such as a cell membrane Preferably, the osmolytic agent or osmolyte is a betaine or carnitine compound.

As used herein a "betaine compound" is any compound than contains a betaine chemical group and is applicable for administration to the eye. Typically, the betaine compound has a molecular weight of about 600 Da or less. Preferably, the betaine compound has a molecular weight of about between 60 and 600 Da. More preferably, the betaine compound has a molecular weight of about 250, 200 or 150 Da or less. Particularly preferred betaine compounds include trimethylglycine, proline betaine, betaine hydrochloride, beta-alanine betaine, hydroxyproline betaine, cocamidopropyl betaine, betaine lipids, betaine esters (for example carbethoxymethyltrimethylammonium hydroxide) or betaine amides. Structural analogs of betaine are also contemplated as suitable for use in the invention provided they exhibit osmoprotectant properties. Examples of such structural analogs include choline-O-sulfate and dimethylsulfoniopropionate (DMSP).

Betaine is a zwitterionic quaternary ammonium compound that is also known as trimethylglycine (TMG), glycine betaine, lycine, and oxyneurine. It is a methyl derivative of the amino acid glycine with a formula of $(CH_3)_3N^+CH_2COO^-$ and a molecular weight of 117.2, and it has been characterized as a methylamine because of its 3 chemically reactive methyl groups. Betaine is found in microorganisms, plants, and animals and is a significant component of many foods including wheat, shellfish, spinach, and sugar beets. Betaine is synthesized from choline by choline oxidase (when choline donates one of these groups to another molecule, it becomes Trimethylglycine betaine) and it can donate methyl groups to homocysteine to form methionine. Betaine is also indirectly involved in the synthesis of carnitine, which is required for transporting long chain fatty acids across the inner mitochondrial member for oxidation. In one embodiment, a "betaine compound" does not include cocamidopropyl betaine.

Two major forms of betaine applied in clinic and health are described below.
 (1) Trimethylglycine—pure form of betaine; and
 (2) Betaine hydrochloride (Betaine HCl).

As used herein a "carnitine compound" is a compound known as 3-hydroxy-4-(trimethylazaniumyl)butanoate or vitamin Bt. Carnitine comes in 2 stereoisomeric forms L-Carnitine and D-Carnitine. L-Carnitine plays an active role in metabolic processes, while the D-carnitine does not have any effects. Carnitine in the form of Acetyl-L-carnitine is used in the treatments for Alzheimer's disease as it positively affects the cholinergic system, the dopaminergic and the NMDA receptor system. L-Carnitine L-Tartarate is more bio-available and faster absorbed than other forms of L-carnitine. A "carnitine compound" is typically has a molecular weight of 300 Da or less. A "carnitine compound" also includes alkanoyl L-carnitines including those selected from the group consisting of acetyl, propionyl, isovaleryl, butyryl, and isobutyryl L-carnitine and their pharmaceutically acceptable salts. Structural analogs of carnitine are also contemplated as suitable for use in the invention provided they exhibit osmoprotectant properties.

As used herein "high tear film tonicity" includes a tear film with a measurable osmolarity of greater than 200 mOsm, preferably greater than 300 mOsm, 400 mOsm or 500 mOsm. Typically high tear film tonicity is between 300 to 500 mOsm, even more preferably between 320 and 400 mOsm.

Tear osmolarity is currently measured from the inferior meniscus and ranges from approximately 300 to 310 mOsM/kg in normal eyes. A diagnosis of dry eye may occur at greater than 310 mOsM/kg, preferably, greater than 311, 312, 313, 314, 315 or 316 mOsM/kg. However, tear hyperosmolarity in individual patients with dry eye may reach as high as 360 to 400 mOsM/kg.

Osmolarity measurements are based on the determination of one of the four colligative properties of a solution: freezing point, boiling point, vapour pressure and osmotic pressure. Freezing point osmometers rely on the correlation between osmolarity and the depression in freezing point by addition of solute to the solvent. Measurements via vapour pressure depression are based on the correlation between osmolarity and the depression in vapour pressure by addition of solute to the solvent. With both freezing point and vapour pressure techniques, the osmolarity measurements are obtained from collected tear samples. The tear sample size varies from 5-20 μL depending on the model of the osmometer. A 'chip-based osmometer' allows in vivo measurements. It simultaneously collect and analyse the electrical impedance of a 50 nanoliter tear sample (TearLab™ Osmolarity System).

Ocular discomfort is commonly measured through questionnaires. The most used approach is asking a subject to rate their ocular comfort by a numeric rating scale which presents the person with a numbered scale eg 1-10 or 1-100 and there are usually descriptions for what 1 means or what 10 or 100 means—generally 1=poor, bad etc and 10/100=good or excellent. These are popular due to it being easy to understand and easy to use and it is something used commonly in other areas of people's lives as well. Other subjective scales include likert scales which usually give a forced 5 choice answer to a question/statement—generally: Strongly agree, Agree, Neither agree or disagree, Disagree or Strongly disagree. There are also visual analogue scales (VAS) which allows a person to draw a vertical line onto a pre-determined horizontal line to indicate their current comfort.

Ocular discomfort may be determined clinically in relation to diagnosed dry eye by measuring tear break up times, tear volumes, corneal staining etc.

The terms "therapeutically effective amount" or "effective amount" refer to an amount of a betaine and/or carnitine compound, that results in an improvement or remediation of the symptoms of ocular discomfort, prevents ocular discomfort, improves ocular comfort or ameliorates decrease in ocular comfort.

The term "pharmaceutical composition" or "composition" refers to a composition comprising a betaine and/or carnitine compound which is dispersed in a pharmaceutically acceptable carrier. The composition may further include one or more additional excipients, such as diluents, emulsifiers, buffers, stabilizing agents, binders, fillers, and the like. A pharmaceutical composition of the invention may include two or more betaine compounds, e.g. trimethylglycine and proline betaine, or two or more carnitine compounds, e.g. L-carnitine and acetyl-L-carnitine.

The term "ophthalmic device" refers to an object that resides in or on the eye. The device may provide optical correction, physical correction (e.g. excessively curved or protruding cornea), or may be cosmetic. Ophthalmic devices include but are not limited to soft contact lenses, intraocular lenses, overlay lenses, ocular inserts, punctual plugs, and optical inserts. The preferred ophthalmic devices of the invention are soft contact lenses made from silicone elastomers or hydrogels, which include but are not limited to silicone hydrogels, and fluorohydrogels. The ophthalmic devices may be "single-use" devices e.g. single-use contact lenses (either daily or extended wear), or "multiple-use" devices, e.g. multiple-use contact lenses.

The term "preventing ocular discomfort" refers to averting, delaying or reducing in frequency and intensity the signs and/or symptoms associated with ocular discomfort (such as dryness and irritation) in a person desiring to wear an ophthalmic device. The term "preventing" is used herein in a clinical sense to mean inhibit discomfort occurring, rather than in an absolute sense of making it impossible for the discomfort to ever occur in a given subject. Therefore, inhibition of progression to discomfort or reduced new discomfort amounts to "prevention" within the meaning of this specification even if there is pre-existing discomfort. The term "improving ocular comfort" refers to increasing the ocular comfort of a person wearing an ophthalmic device by decreasing symptoms such as dryness and irritation. The term "reducing ocular discomfort" or "ameliorating ocular discomfort" refers to decreasing symptoms such as dryness and irritation, particularly in a person wearing an ophthalmic device. The term "ameliorating decrease in ocular comfort" refers to avoiding or minimising an increase in ocular discomfort of a person wearing an ophthalmic device.

In one embodiment of the invention a diffusion attenuator is include in the ophthalmic device to affect the release of the betaine and/or carnitine compound from the device. While any compound that is suitable for application to the eye and which reduce the rate at which a betaine and/or carnitine compound can diffuse from an ophthalmic device is contemplated, a particularly useful diffusion attenuator is vitamin E. Examples of contact lenses that include vitamin E and a description of their preparation can be found in WO 2009/094466, the disclosure of which is incorporated by reference in its entirety.

In an alternative embodiment, the pharmaceutical compositions according to the present invention will be formulated for administration to the eye e.g. an eye drop or a spray.

The device or composition of the present invention and another active ingredient may be administered at the same time (either in the same or different compositions) or at times close enough such that the administration results in an overlap of the desired effect. Alternatively, the composition of the present invention may precede or follow other treatments. For example, an ophthalmic device of the invention that includes a betaine compound may be used by a subject who then concurrently administers a composition including a carnitine compound. Alternatively, the ophthalmic device of the invention that includes a carnitine compound may be used by a subject who then concurrently administers a composition including a betaine compound.

A kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a betaine compound and/or a carnitine compound, an ophthalmic device of the invention or a pharmaceutical composition of the invention which is effective for treating the condition and may have a sterile access port. The label or package insert indicates that the betaine compound and/or carnitine compound, ophthalmic device of the invention or pharmaceutical composition is used for treating the condition of choice. In one embodiment, the label or package insert includes instructions for use and indicates that the betaine compound and/or carnitine compound, ophthalmic device of the invention or pharmaceutical composition can be used to inhibiting, ameliorating or reducing ocular discomfort associated with high tear film tonicity.

A kit may comprise (a) an ophthalmic device of the invention or a pharmaceutical composition of the invention; and (b) a second container comprising a solution that is suitable for application to the eye, carriers, excipients, other active ingredients and the like. The kit in this embodiment of the invention may further comprise one or more package inserts. The inserts may, for example, indicate that the ophthalmic device of the invention or pharmaceutical composition can be used to inhibiting, ameliorating or reducing ocular discomfort associated with high tear film tonicity, and provide instructions for use of the kit. The second container may comprise a solution that is suitable for application to the eye (e.g. an aqueous solution) and/or pharmaceutically-acceptable buffers, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The invention also provides a solution for adding a therapeutically effective amount of one or more betaine compounds and/or one or more carnitine compounds to a ophthalmic device, the solution including a betaine and/or a carnitine compound and a physiologically acceptable carrier, dliuent or excipient. Typically, a betaine compound and/or a carnitine compound is present in the solution at about 5 to 100 mM, preferably about 5 to 50 mM, even more preferably 20 mM. Typically, the carrier, dliuent or excipient facilitates the addition of one or more betaine compounds and/or one or more carnitine compounds to the ophthalmic device.

Aqueous solutions are generally preferred for topical administration, based on ease of formulation, as well as a subject's ability to easily administer such compositions by means of instilling one to two drops of the solutions in the affected eyes. However, the compositions may also be suspensions, viscous or semi-viscous gels, or other types of solid or semi-solid compositions, or those appropriate for sustained release.

The "solutions" that are used in methods of this invention may be water-based (i.e. aqueous) solutions. Typical solutions include saline solutions, other buffered solutions, and deionized water. The preferred aqueous solution is deionized water or saline solution containing salts including sodium chloride, sodium borate, sodium phosphate, sodium hydrogenphosphate, sodium dihydrogenphosphate, or the corresponding potassium salts of the same. These ingredients are generally combined to form buffered solutions that include an acid and its conjugate base, so that addition of acids and bases cause only a relatively small change in pH. The buffered solutions may additionally include 2-(N-morpholino)ethanesulfonic acid (MES), sodium hydroxide, 2,2-bis(hydroxymethyl)-2,2',2"-nitrilotriethanol, n-tris(hydroxymethyl)methyl-2-aminoethanesulfonic acid, citric acid, sodium citrate, sodium carbonate, sodium bicarbonate, acetic acid, sodium acetate, ethylenediamine tetraacetic acid and the like and combinations thereof. Preferably, the solution is a borate buffered or phosphate buffered saline solution or deionized water. The particularly preferred solution contains about 8 g/L NaCl, 0.2 g/L KCl, 1.15 g/L $Na_2HPO_4$ and 0.2 g/L $KH_2PO_4$ buffer.

Any of a variety of carriers may be used in the compositions of the present invention including water, mixtures of water and water-miscible solvents, such as $C_1$- to $C_7$-alkanols, vegetable oils or mineral oils comprising from 0.5 to 5% non-toxic water-soluble polymers, gelling products, such as gelatin, alginates, pectins, tragacanth, karaya gum, xanthan gum, carrageenan, agar and acacia, and their derivatives, starch derivatives, such as starch acetate and hydroxypropyl starch, cellulose and its derivatives and also other synthetic products, such as polyvinyl alcohol, polyvinylpyrrolidone, polyvinyl methyl ether, polyethylene oxide, preferably cross-linked polyacrylic acid, such as neutral Carbopol, or mixtures of those polymers, naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan mono-oleate.

For the adjustment of the pH, preferably to a physiological pH, buffers may especially be useful. The pH of the present solutions should be maintained within the range of 4 to 8. It will be understood by a person of ordinary skill in the art that any pH that is compatible with the ocular surface is suitable. Suitable buffers may be added, such as boric acid, sodium borate, potassium citrate, citric acid, sodium bicarbonate, TRIS, disodium edetate (EDTA) and various mixed phosphate buffers (including combinations of $Na_2HPO_4$, $NaH_2PO_4$ and $KH_2PO_4$) and mixtures thereof. Generally, buffers will be used in concentrations ranging from about 0.05 to 0.5 M.

It will be understood that the invention disclosed and defined in this specification extends to all alternative combinations of two or more of the individual features mentioned or evident from the text or drawings. All of these different combinations constitute various alternative aspects of the invention.

EXAMPLES

The present invention will now be more fully described with reference to the accompanying examples and drawings. It should be understood, however, that the description following is illustrative only and should not be taken in any way as a restriction on the generality of the invention described above.

Example 1

An immortalized human corneal limbal epithelial (HCLE) cell line (a kind gift from Ilene Gipson, Schepens Eye Research Institute, Boston, Mass.) was used in the study. HCLE cells were cultured as previously described (Garrett et al. *Invest Ophthalmol Vis Sci* 2008; 49:4844-4849). Briefly, the cells were maintained on plastic at $2\times10^4/cm^2$ in a keratinocyte serum-free medium (K-SFM; Invitrogen-Gibco, Grand Island, N.Y.), supplemented with 25 μg/mL bovine pituitary extract, 0.2 ng/mL epidermal growth factor (EGF; Invitrogen, Mount Waverley, VIC, Australia), and 0.4 mM $CaCl_2$ and were grown at 37° C. in a 5% carbon dioxide atmosphere. To enhance nutrient composition, the cultures were switched at approximately 50% confluence to a 1:1 mixture of K-SFM and low calcium DMEM/F12 (Invitrogen), to achieve confluence. All the experiments involving the culture of HCLE cells were performed at 37° C. in a 5% carbon dioxide atmosphere unless otherwise indicated.

To determine the optimal concentration of betaine for use in the osmoprotective studies, betaine (Sigma-Aldrich, St. Louis, Mo.; 1.0-200 mM) was prepared in culture medium. Cells were plated at a density of $5\times10^4$ cells $mL^{-1}$ and grown until 80% confluence then exposed to culture medium with osmolarity of 300 mOsm in the presence or absence of betaine for 16 h. Following treatment with betaine, cell viability was assessed using the 3-[4,5-dimethylthiazol-2-yl]-2,5-diphenyltetr azoliumbromide (MTT) cell survival assays (Promega, Madison, Wis.).

Forward scatter of the laser light produced by the flow cytometer is proportional to the volume of the cell. This principle was used to analyse the osmoprotective effect of betaine in restoring the cell volume which is adversely affected due to hypertonicity. Cell populations were gated such that the population of cells showing a greater forward scatter (FSC) constituted the percentage of cells with a volume equal to that of a cell under isotonic conditions. On the other hand, the proportion of side scatter in a flow cytometer represents the cell structure complexity and granularity. Thus the population of cells exhibiting greater side scatter (SSC) represents cells with reduced volume. Cells were exposed to isotonic media (300 mOsM), hyperosmotic media (500 mOsM) and hyperosmotic media containing betaine (500 mOsM media+10 mM betaine) for 16 h after which they were analysed using flow cytometer.

Cell volume and Live/Dead staining via flow cytometry were performed using the Attune® Acoustic focusing Cytometer (Life Technologies™ Applied Biosystems). Annexin V and PI kit (Invitrogen™) was used to analyse the non-apoptotic, and the early and late apoptotic cells. Staining was performed as per manufacturer's instructions. Analysis of Annexin staining was conducted using the blue/violet laser with excitation/emission spectra of 480/500 nm (20 mW) and the PI staining analysis was conducted using blue/red laser with an excitation/emission spectra of 490/635 nm.

500 mOsm and exposure time (16 h) to be the most informative under which to observe hyperosmolality induced cellular responses of HCLE (results not shown). Thus, in the present study, a hyperosmotic medium of 500 mOsm and exposure time of 16 h were used throughout. Hyperosmolar media were prepared by the addition of NaCl to the medium. Medium osmolarity was measured using a Vapro 5520 vapour pressure osmometer (Wescor, Logan, Utah). Subconfluent cells were exposed to hyperosmolar media in the presence or absence of betaine (5 or 10 mM). Mitochondrial and proliferation activities for cell viability; TNF-α production; caspase activity and Annexin V/PI staining for apoptosis; and cellular shrinkage were monitored as detailed below.

It was observed that an osmolarity of 450 mOsM and 500 mOsM and exposure time of 16 hours was the most optimal for studying hyperosmolarity induced cellular responses of HCLE (results not shown). Therefore, a hyperosmolar medium of 450 mOsM and 500 mOsM and an exposure time of 16 hours were used throughout the study. The hyperosmolarity of the medium was achieved by addition of an appropriate amount of NaCl to it, and further measuring using Vapro 5520 vapor pressure osmometer (Wescor, Logan, Utah). Cells, having reached 70%-80% confluence were exposed to hyperosmolar media in the presence or absence of 10 mM L-Carnitine. Cellular shrinkage in relation to hyperosmotic stress, Annexin V/PI staining for apoptosis, Caspase activities and TNF-α production were analysed.

MTT viability assay kit was used to measure cell viability (above). CyQUANT cell proliferation assay kit (Invitrogen-Molecular probe, Eugene, Oreg.) was used to determine the cell number. Culture supernatants were removed and centrifuged at 1500 rpm for 10 min to harvest any detached cells from the supernatant. Remaining cells were rinsed once with PBS. Lysis buffer containing CyQUANT GR dye was added to the cells including cells harvested from supernatant and incubated for 2-5 minutes at room temperature. Fluorescence, indicating cell viability, was measured using SpectraFluor Plus microplate reader (Tecan, Männedorf, Switzerland); 485 nm for excitation and 535 nm for emission maxima.

Enzyme-linked immunosorbent assay (ELISA) was used to quantify TNF-α. The culture supernatants were collected, centrifuged at 1500 rpm for 10 min to remove cellular debris and stored at −80° C. until processed. Assays were performed according to manufacturer's protocol (R&D Systems, Minneapolis, Minn.).

Caspase-3/7, -8 and -9 activities were assayed using a luminescent assay kit (Promega, Madison, Wis.) according to the manufacturer's instructions. Briefly, 100 μL of Caspase-Glo-3/7, -8 and -9 reagents were added to HCLE at maintained on plastic at $2 \times 10^4$/cm$^2$, mixed and incubated for one hour at room temperature. Luminescence was measured using a SpectraFluor Plus microplate reader.

Cells undergoing apoptosis or necrosis were identified using Alexa Fluor 488 annexin V/Dead cell apoptosis assay (Invitrogen-Molecular probe) with some modifications. Cells were seeded at $6.5 \times 10^4$ cells mL$^{-1}$ in 75 cm$^2$ cell culture flask and incubated overnight. Once the cells reached 70%-80% confluence, they were subjected to different osmolarity treatments for 16 hours. Supernatants were removed and retained for collection of non-adherent cells. Adherent cells were rinsed twice with PBS and detached using 0.05% trypsin. The culture supernatant and trypsin digests were pelleted, rinsed twice in PBS, and combined during resuspenison in annexin-binding buffer. Five microlitres of Alexa Fluor 488 annexin V, 12.5 μg mL$^{-1}$ of Hoechst 33342 and 1 μg mL$^{-1}$ of propidium iodide (PI) were added to 100 μL of cell suspension containing approximately $1 \times 10^5$ cells and incubated at room temperature for 15 minutes. Cells were washed with 200 μL of annexin-binding buffer and deposited onto coverslips. Images were captured using FluoView FV1000 confocal laser scanning microscopy (Olympus, Japan) with 7-10 images of different fields of view being captured for each treatment. Cells stained with annexin V, PI or Hoechst for apoptotic, necrotic or total cells, respectively, were quantified for each image using ImageJ (http://rsbweb.nih.gov/ij/; National Institutes of Health, Bethesda, Md.) to obtain an average value for each treatment.

All results are presented as mean±SD. Group means were compared by one way analysis of variance (ANOVA) using Bonferroni correction. The Student's t-test was performed for comparison of data comprising two groups at the $p<0.05$ level of significance.

All the lenses are dried in the air overnight and weighed after dehydration. The dried lenses are soaked in 3 ml solution of vitamin E in ethanol. Several concentrations are chosen to obtain a calibration curve for % loading in gel as a function of the vitamin E concentration in ethanol. The lenses are dried in the air overnight, and weighed to determine the vitamin E loading in the lenses.

After the lenses are loaded with the desired amount of vitamin E, the lenses are transferred into dexpanthenol (8 mg/ml and 3 ml in volume) or betaine (80 mg/ml and 3 ml in volume) for drug loading. The drug loading is conducted for at least 20 hours (some lenses were soaked in drug solution up to 3 days but no significant difference was detected). The control lenses (no Vitamin E) are also loaded with the drugs by following the same approach.

The drug loaded lenses are submerged in 2 ml of fresh PBS for the drug release experiments. The drug concentration is measured periodically by UV Vis spectrophotometer.

Each experiment for each type of lens (both pure and vitamin E loaded) was conducted at least in triplicate.

Titration of betaine concentrations ranging from 0 mM to 200 mM determined that betaine up to 40 mM was not toxic to the cells (FIG. 1). Further it was found that betaine at up to 10 mM had minimal effect on the final osmolarity of the medium (results not shown). Therefore, 5 and 10 mM betaine were the concentrations chosen for further testing.

Cell viability analysis was carried out to analyse the toxicity of various concentrations of L-Carnitine and it was found that 10 mM L-Carnitine concentration was optimal to carry out osmoprotective studies.

Example 2

Flow cytometry analysis was performed to determine the physiological state of the cells (FIG. 2A) and cell volume (FIG. 2B) in response to hyperosmotic stress in the presence or absence of betaine. The representative images of the HCLE cells exposed to isotonic medium, hyperosmolar medium and hyperosmolar medium+10 mM betaine (FIG. 2A(I)) revealed that the total percentage of apoptotic and necrotic cells was considerably increased during exposure to hyperosmotic conditions as compared to isotonic conditions (from 8.24% to 29.63%) In the presence of the osmoprotectant betaine, the number of damaged cells was reduced dramatically (from 29.63% to 15.70%) This observation was further confirmed in the experiment summarised in FIG. 2A (II) which shows the percentage reduction in healthy cells under hyperosmotic stress compared to isotonic conditions ($p<0.05$). Addition of betaine to the hyperosmotic medium maintained the percentage of viable cells to levels similar to those observed under isotonic conditions.

The population of shrunken cells markedly increased when the cells were subjected to hyperosmolar conditions compared with populations subjected to the isotonic environment (from 4.73% to 26.82%). The population of shrunken cells reduced in number when the cells were treated with 10 mM betaine in hyperosmotic media (from 26.82% to 11.01%) effectively restoring cell volume to that observed under isotonic conditions. FIG. 2(II) further confirmed that hyperosmotic stress resulted in a significant reduction in population of cells of normal (isotonic) volume compared to isotonic control populations (p<0.05). Addition of betaine to the hyperosmotically stressed cell population counteracted this reduction.

Flow cytometry analysis was used to determine the cell volume in response to hypertonicity with our without L-Carnitine. The representative images of HCLE cells exposed to isotonic medium, hypertonic medium and hypertonic medium along with 10 mM L-Carnitine indicate that the percentage of cells showing compromised cell volume dramatically increased under hyperosmotic stress as compared to those in the isosmotic conditions (From >4.0% to >30.0%). On the other hand, when additionally supplemented with L-Carnitine, the cells under hyperosmotic stress, showed considerably lower percentage of shrunken cells similar to that observed under isotonic conditions (18.01%). This reduction in the number of shrunken cells when treated with 10 mM Carnitine in hyperosmotic media effectively indicated the role of L-Carnitine in restoration of cell volume.

Figure 3A:
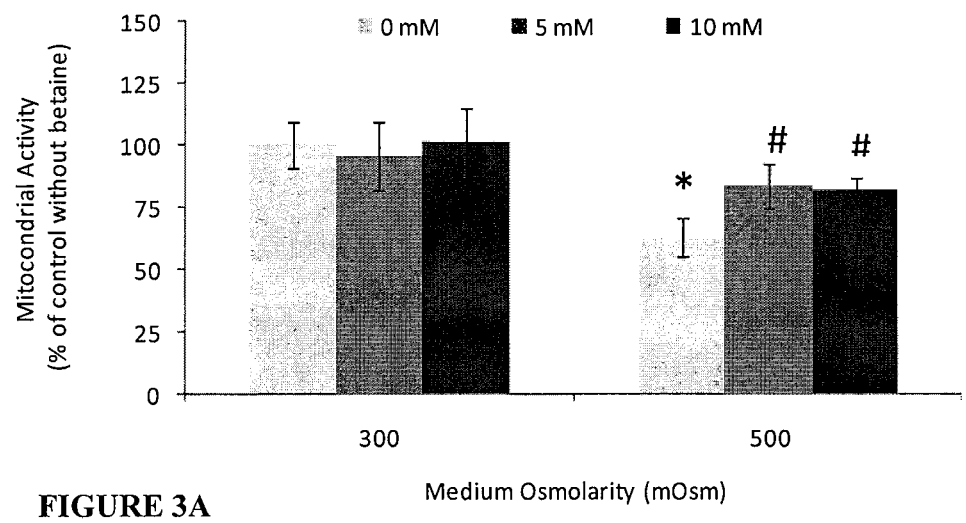
FIGS. 3A and 3B. Effect of betaine on HCLE cells exposed to hyperosmolar medium for 16 h: (A) cellular mitochondrial activity; and (B) cell number. Data are shown as mean±SD (n=10) percentage compared to untreated isotonic (300 mOsm) medium group. * Significant difference between cells treated with isotonic 300 mOsm and hyperosmotic 500 mOsm. #Significant difference between cells treated with and without betaine in 500 mOsm (p<0.05).
Figure 3B:
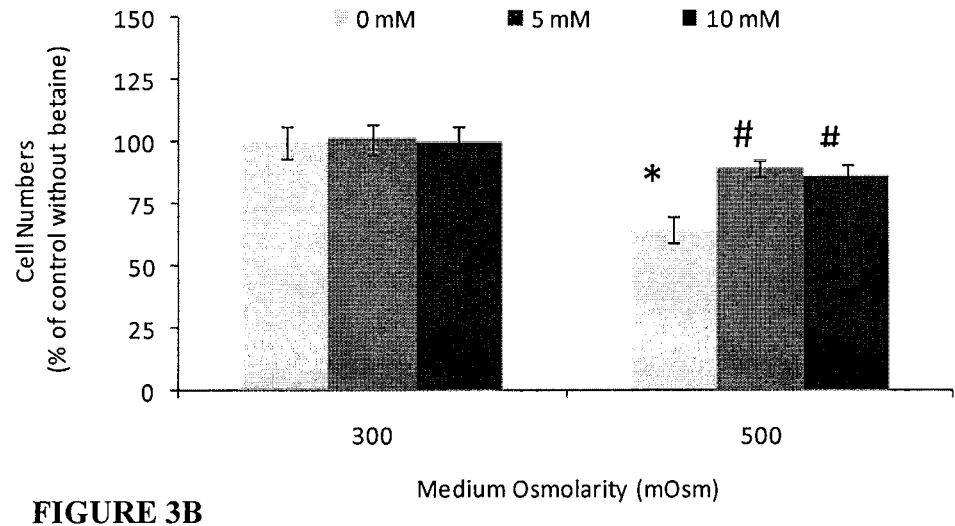

Mitochondrial activities, indicating cell viability (FIG. 3A), and cell number (FIG. 3B) were assessed following exposure to hyperosmolar media with or without betaine. Compared to isotonic medium, exposure to hyperosmolar medium without betaine resulted in reduction in mitochondrial metabolic function by 38% as assessed by MTT assay, and in cell numbers by 35% as assessed by CyQuant proliferation assay (p<0.05). However, cells exposed to hyperosmolar medium containing 5 or 10 mM betaine exhibited significantly higher survival with increases in mitochondrial activity and cell numbers of 17% and 12% respectively, which was significantly different compared to the hyperosmotic control (without betaine treatment; p<0.05).

Figure 4:
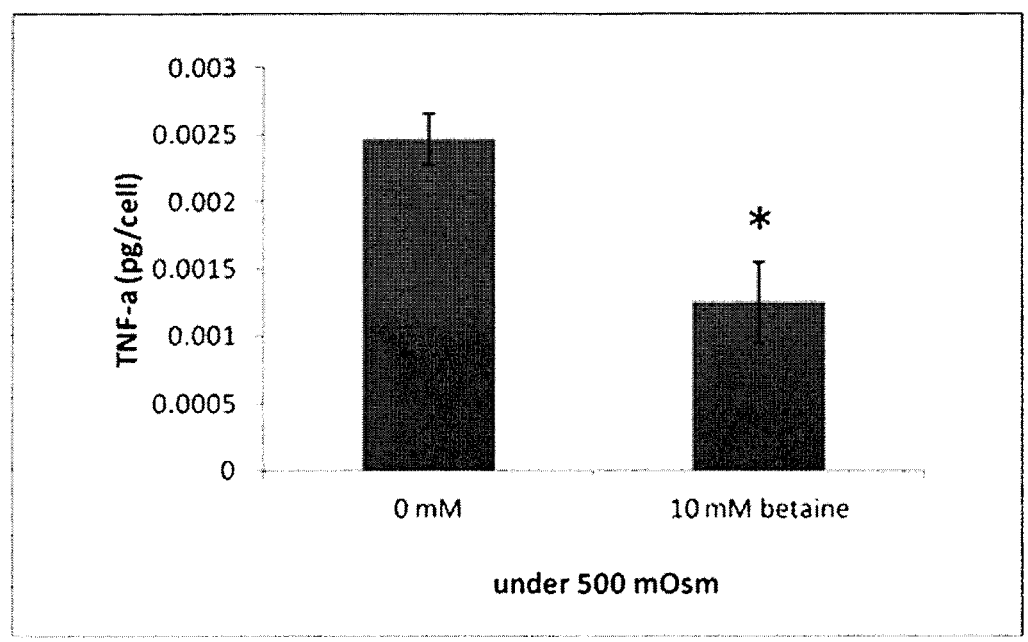
FIG. 4. Production of TNF-α by HCLE cells after exposed to hyperosmolar medium (500 mOsm) with or without betaine (10 mM) for 16 h. Data represents mean±SD of five samples. *Shows statistical significant difference compared to the control without betaine (p<0.05).

TNF-α expression was measured in culture supernatants following exposure to hyperosmolar medium with or without betaine (10 mM) (FIG. 4). TNF-α was barely detectable in control samples (300 mOsm) (results not shown). Comparison of betaine-treated samples in hyperosmolar medium media to samples without betaine (FIG. 4, p<0.05) showed a 40% reduction in TNF-α levels.

Figure 5A:
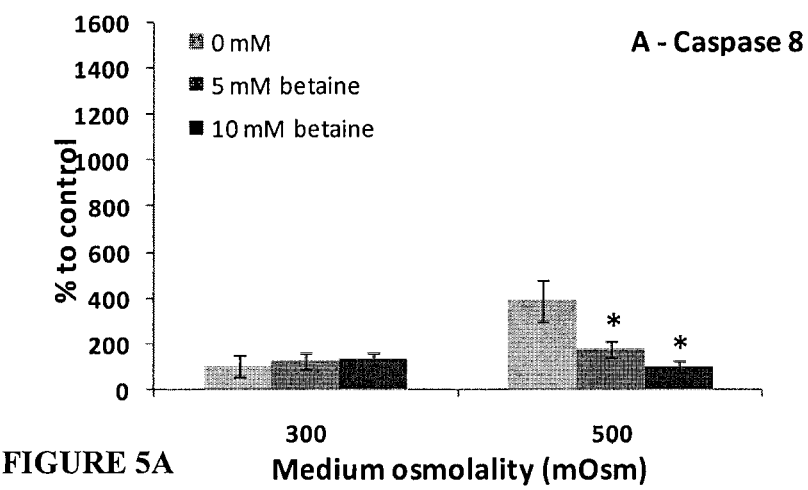
FIGS. 5A, 5B, and 5C. HCLE caspase activities in response to hyperosmotic stress and treatment with betaine (5 or 10 mM) after cells were exposed to isotonic (300 mOsm) or hypertonic medium (500 mOsm) for 16 h in the presence or absence of betaine: (A) caspase-8; (B) caspase-9; and (C) caspase-3/7. Data are shown as percentage mean±SD (n=6) over their respective isotonic medium group (300 mOsm). * Significant difference between cells treated with and without betaine for exposure to the same medium osmolarity (p<0.05).
Figure 5B:
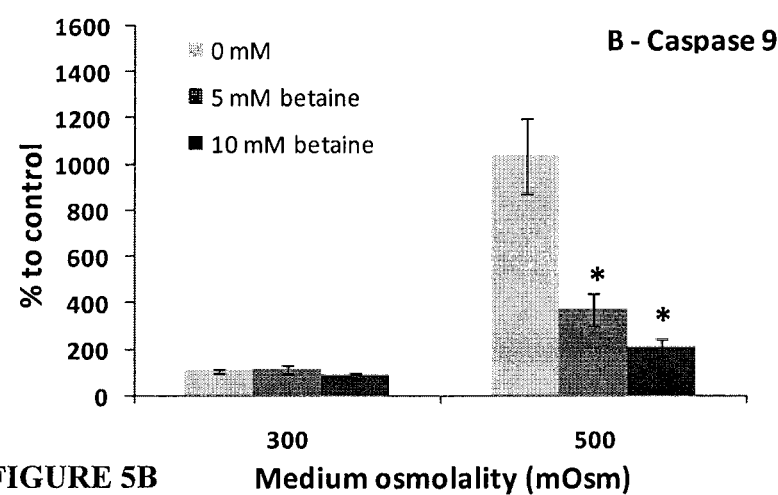
Figure 5C:
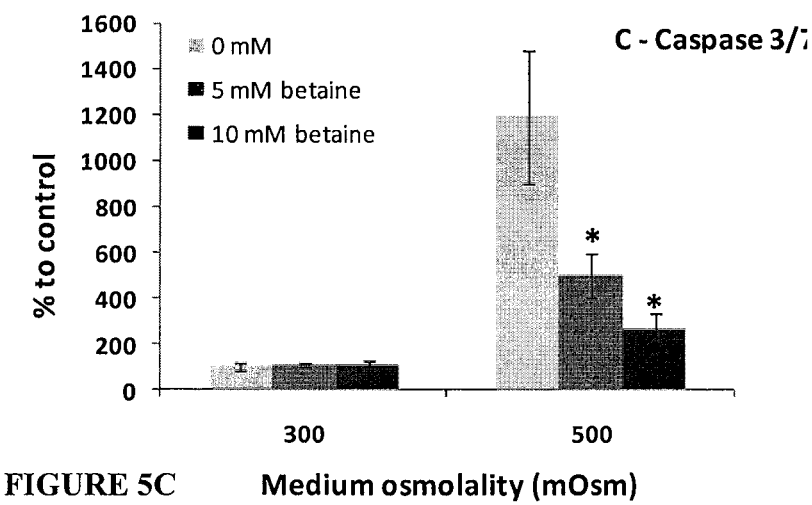
Figure 7A:
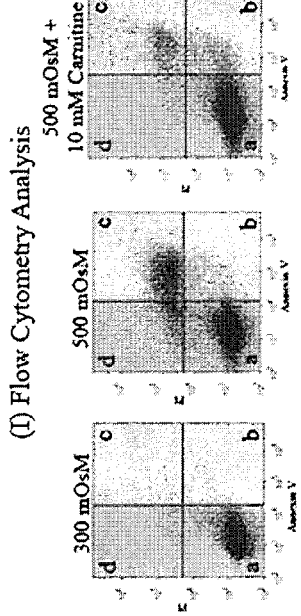
FIGS. 7A and 7B. Flow cytometry analysis of the cellular responses to hyperosmotic shock in the presence or absence of carnitine (10 mM).
Figure 7A:
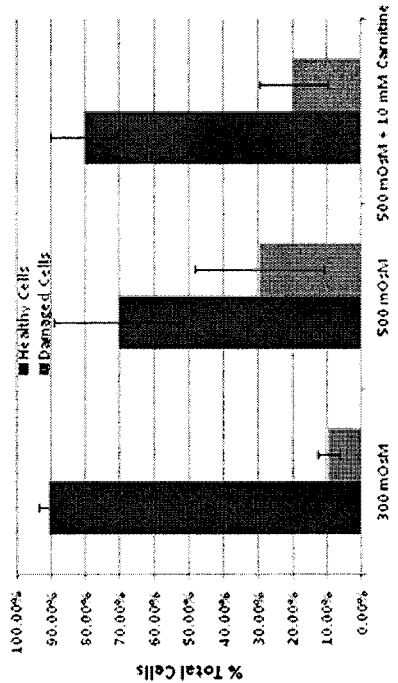
Figure 7A:
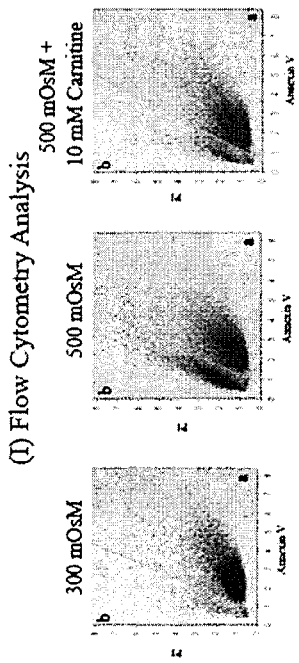
Figure 7B:
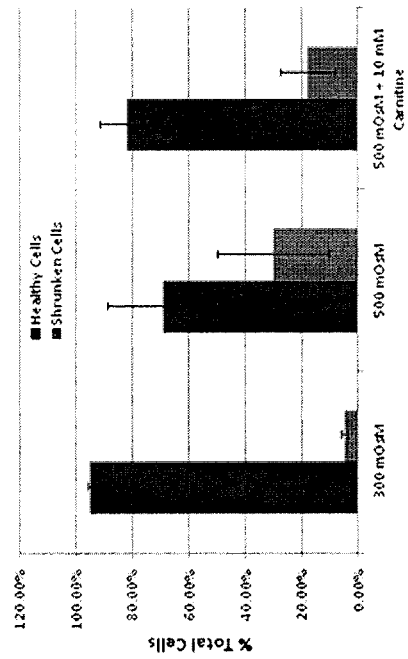

The effect of betaine on HCLE caspase activities, a specific indicator of the apoptotic process, was further delineated following exposure to osmotic stress (FIG. 5). When exposed to hyperosmolar medium, levels of caspases-8, -9 and -3/7 activities in the betaine-treated group, either at 5 or 10 mM, were significantly lower than controls without betaine-treatment (p<0.05). Approximately 2- to 3-fold reduction in the presence of 5 mM betaine and 4- to 5.2-fold reduction in the presence of 10 mM betaine were observed for all the caspase activities measured (caspase-8, -9 and -3/7).

The up-regulation in the activities of caspases in the mammalian cells specifically indicates the outset of the apoptotic processes. To confirm the deleterious effects of hyperosmolarity and the osmoprotective characteristic of Carnitine observed in the flow cytometry the Caspase activities were further examined following 16 hour exposure to hyperosmotic stress. When exposed to hypertonic medium, the levels of Caspases-8, -9 and -3/7 activities dramatically increased. The Carnitine treated controls showed significant lowering in Caspase-9 and -3/7, however showing minimum or no visible decline in the activity of Caspase-8.

The positive osmoprotective effect of betaine was further evidenced in FIG. 6. FIG. 6a shows a dramatic increase in the number of damaged cells (15% of the total cells) following exposure to hyperosmolar medium compared to the isotonic control 300 mOsm (3.8%, p<0.05). However, in the presence of 10 mM betaine, the percentage of damaged cells in response to the hyperosmolar shock significantly reduced to half that of hyperosmolar medium without betaine (7.5%, p<0.05). The damaged cells in the present study were analyzed by confocal microscope at 60× using Annexin V and PI staining and proved to be composed of early apoptotic (FIG. 6b, positive annexin V-immunostaining; late apoptotic (FIG. 6, positive annexin V and PI staining); early and late necrotic (FIGS. 6d and 6e, PI positive) cells. Cell damage induced by hyperosmotic shock, and the osmoprotective effect of betaine, are further demonstrated by the representative images taken at 10× confocal microscope (FIG. 6f-6h) in which an increased population of positively stained cells for both annexin V and PI can be observed in response to hyperosmotic shock without betaine, compared to isotonic \or hypertonic in the presence of 10 mM betaine.

Following the analysis of the volume of the cell, the physiological state of the cells was further analysed with Flow cytometer by performing the Annexin V/dead cell apoptosis assay. The figures below reveal that the percentage of healthy cells considerably declined in the presence of hyperosmolar conditions (>90.0% to >70.0%) and that of the apoptotic and necrotic cells increased as compared to those in the isotonic conditions (~20.0%). However, in the presence of Carnitine, the number of apoptotic and necrotic cells visibly reduced consequently (from ~29.0% to ~19.0%) increasing the percentage of healthy cells showing similarity to those observed in the isotonic conditions, therefore suggesting the osmoprotective role of Carnitine.

Example 3

Cultured HCLE cells were exposed to culture medium with or without carnitine (10 mM) at 300 mOsm (isotonic) and 500 mOsm (hyperosmotic) for 16 h. Flow cytometry was performed to determine the cell volume changes based on the forward and side scatter values detected.

The percentage of shrunken cells significantly increased when the cells were subjected to 500 mOsm hyperosmotic conditions (~27%) compared with populations subjected to the isotonic 300 mOsm environment (~5%) (FIG. 7). However, the percentage of these shrunken cells markedly reduced when the cells were treated with 10 mM carnitine in 500 mOsm hyperosmolar media (~15%). Carnitine is able to regulate cell volume under hyperosmolar stress preventing subsequent apoptosis.

Cultured human corneal limbal epithelial (HCLE) cells were exposed to culture medium with or without carnitine (10 mM) at 300 mOsm (isotonic), 450 mOsm (moderate), and 500 mOsm (hyperosmotic) for 16 h. Induction of apoptosis was detected by quantification of the proteolytic activity of caspase-8, caspase-9, or caspase-3/7 using caspase activity assays, and production of tumor necrosis factor (TNF)-α, a known apoptosis inducer, using ELISA. Annexin V and Propidium iodine (PI) staining was performed to detect the percentage of apoptotic cells using confocal microscopy and flow cytometry.

Figure 8A:
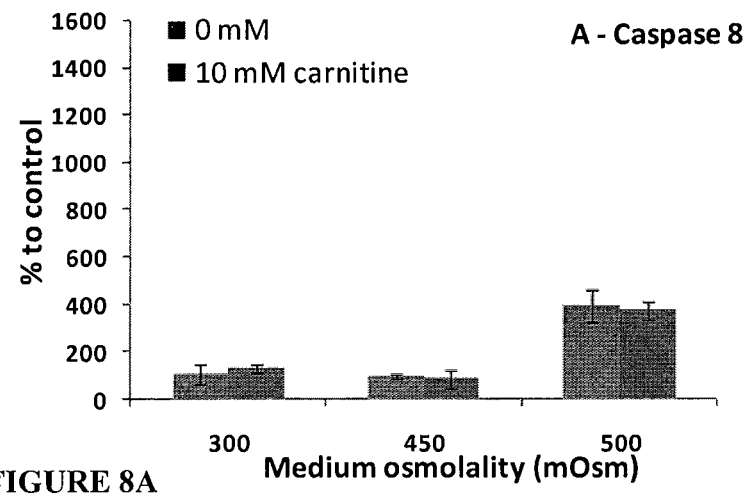
FIGS. 8A, 8B, and 8C. HCLE caspase activities in response to hyperosmotic stress and the treatment with carnitine. Cells were exposed to isotonic (300 mOsm) or hypertonic medium (450 or 500 mOsm) for 16 h in the presence or absence of carnitine (10 mM) (A) caspase-8; (B) caspase-9; and (C) caspase-3/7. Data are shown as percentage mean±SD (n=6) over their respective isotonic medium group (300 mOsm). * Significant difference between cells treated with and without osmoprotectants for exposure to the same medium osmolarity (p<0.05).
Figure 8B:
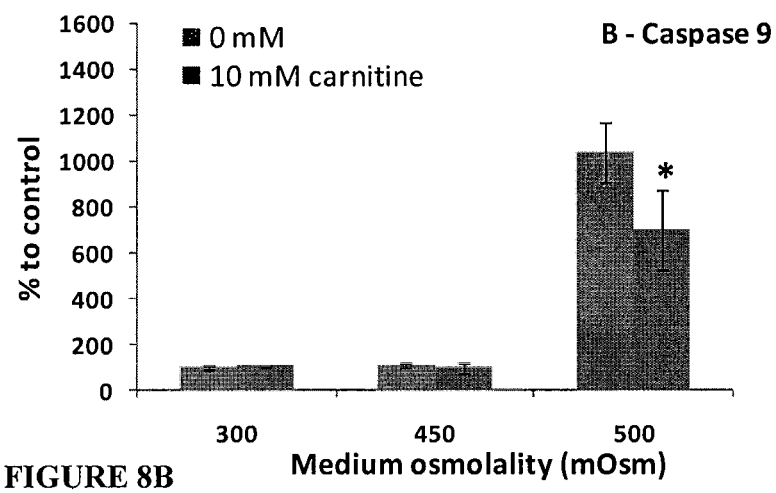
Figure 8C:
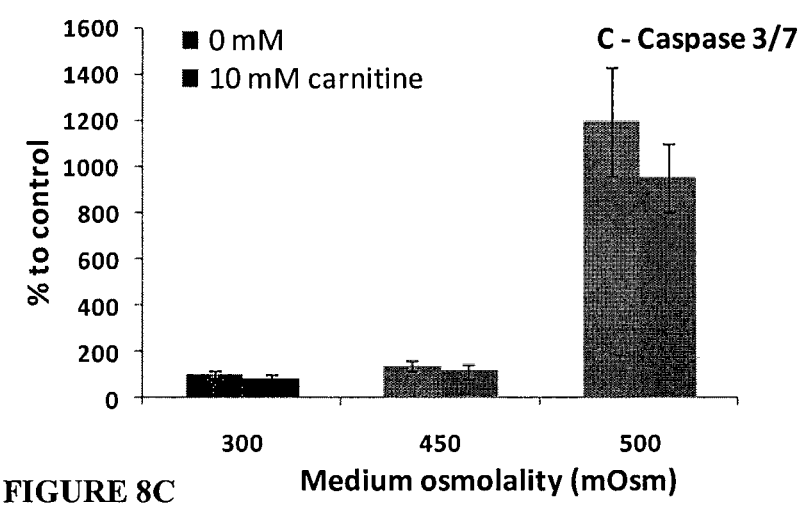
Figure 9:
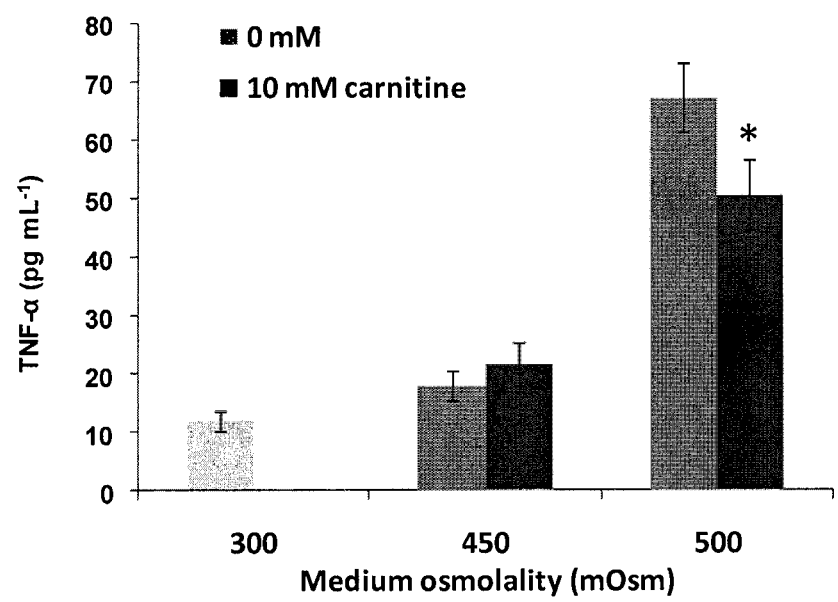
FIG. 9 Production of TNF-α by HCLE cells after exposed to hyperosmolar medium (450 or 500 mOsm) with or without carnitine (10 mM) for 16 h. Data represents mean±SD of five samples. *Shows statistical significant difference compared to their respective control without betaine (p<0.05).

Compared to hyperosmotically stressed HCLE, the presence of carnitine (10 mM) in the hyperosmolar medium (500 mOsm) resulted in significant reduction in cellular caspase-9 activities (33%, p<0.05) and a decreasing trend for caspase-3/7 activities (20%) (FIG. 8); significantly reduced TNF-α production (25%) (p<0.01) (FIG. 9); as well as significant increase in the percentage of un-damaged (non-apoptotic/non-necrotic) cells (63%) (p<0.05), indicating decreased apoptosis in the presence of carnitine. The compatible solute carnitine can inhibit cellular apoptosis of cultured human corneal epithelial cells during hyperosmotic stress.

Example 4

Figure 10A:
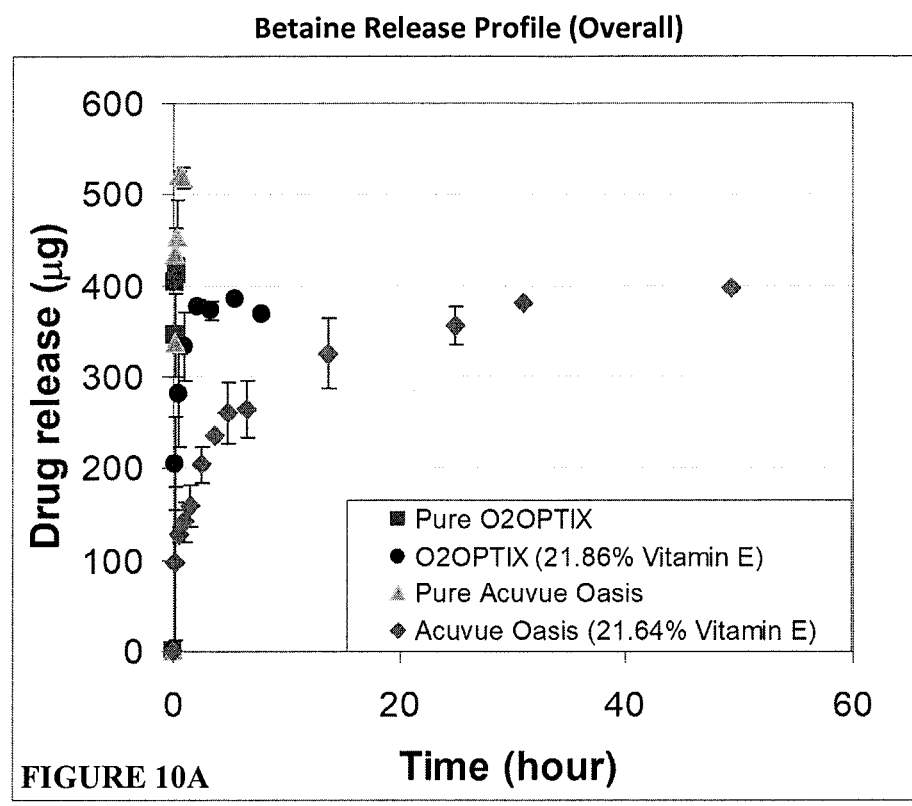
FIGS. 10A and 10B. Release of betaine from O2OPTIX and ACUVUE OASYS lenses with and without Vitamin E over a 60 hour time period (A) or a 10 hour time period (B).
Figure 10B:
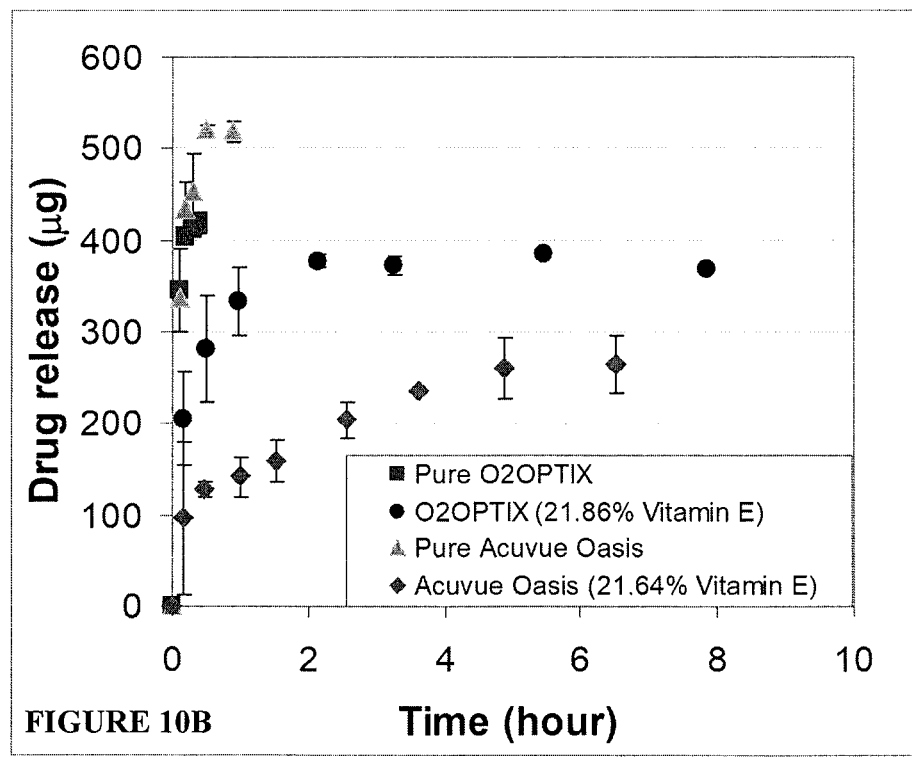
Figure 11A:
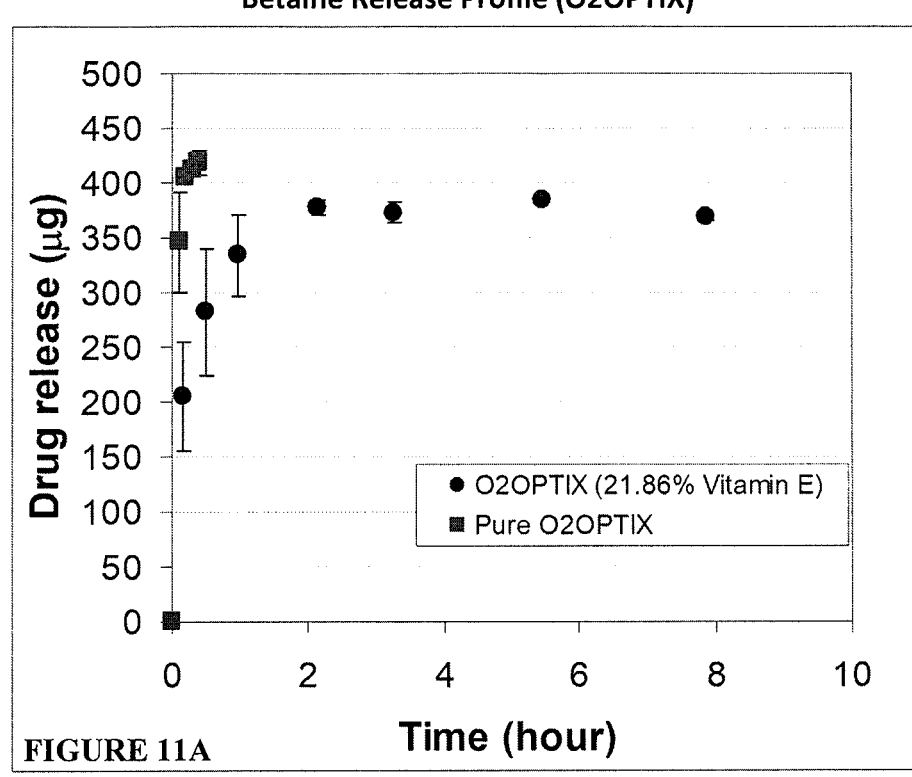
FIGS. 11A and 11B. Release of betaine from O2OPTIX lenses with and without Vitamin E over a 10 hour time period shown as either µg of betaine (A) or % of total betaine (B) released over time.
Figure 11B:
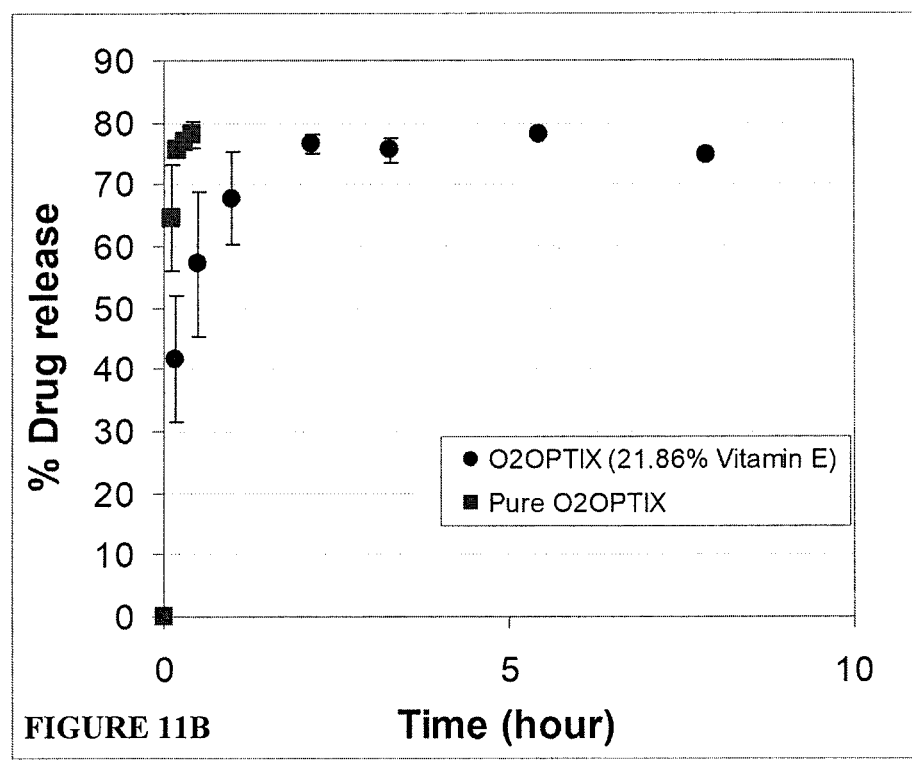
Figure 12A:
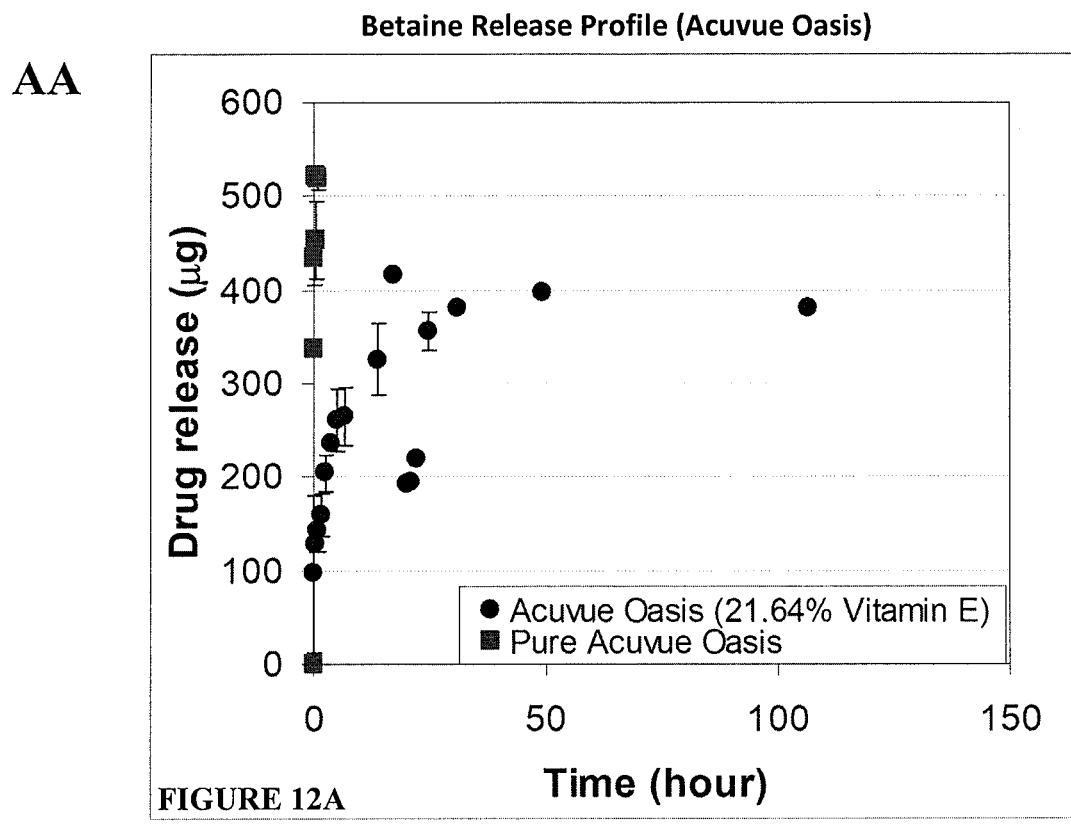
FIGS. 12A and 12B. Release of betaine from ACUVUE OASYS lenses with and without Vitamin E over a 150 hour time period (A) or 60 hour time period (B) shown as either µg of betaine or % of total betaine released over time.
Figure 12B:
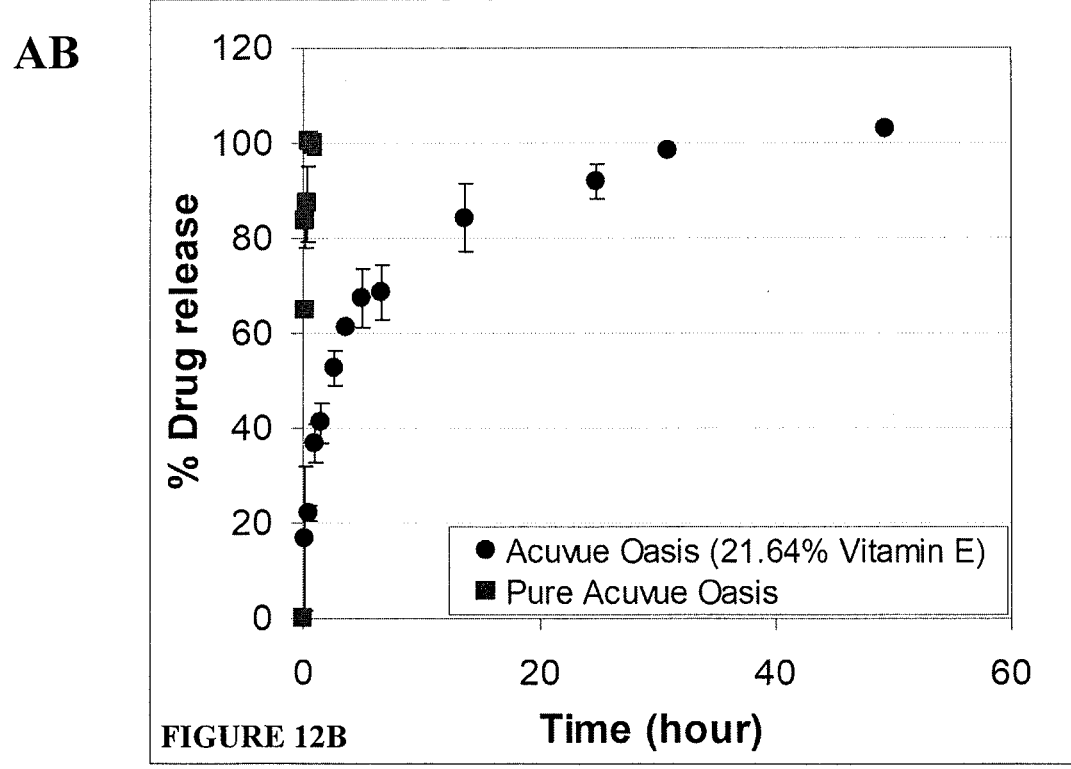

FIG. 10 shows the release of betaine from O2OPTIX and ACUVUE OASYS lenses with and without Vitamin E over a 60 hour time period (A) or a 10 hour time period (B). The presence of vitamin E as a diffusion attenuator slows the release of betaine in each type of contact lens. FIG. 11 shows the release of betaine from O2OPTIX lenses with and without Vitamin E over a 10 hour time period shown as either µg of betaine (A) or % of total betaine (B) released over time. FIG. 12 shows the release of betaine from ACUVUE OASYS lenses with and without Vitamin E over a 150 hour time period (A) or 60 hour time period (B) shown as either µg of betaine or % of total betaine released over time. The presence of vitamin E as a diffusion attenuator slows the release of betaine in each type of contact lens. In other words, a lower amount of betaine is released from a contact lens at any given time in the presence of vitamin E compared to the betaine released from a contact lens without vitamin E.

Example 5

This example illustrates the invention in an animal model.

A total of 110 female C57BL/6 mice (age 4-6 weeks, from the Animal Breeding Unit of Wenzhou Medical College) were used in the study. These mice were carefully selected out of 350 mice by clinical examination using slit-lamp microscopy and corneal staining. Only those healthy mice with no corneal infections, infiltration or leukom, and with total scores of corneal fluorescein staining of less than 10, were selected for the study.

This study used the ICES-induced murine dry eye model in which relative humidity, airflow and temperature were maintained at 15.7±3.2% (mean±SD), 2.1±0.2 m/s and 21-24° C., respectively, and mice began developing dry eye conditions similar to those in humans from Day 21 post-housing (Chen et al A Murine Model of Dry Eye Induced by an Intelligently Controlled Environmental System. *Investigative Ophthalmology & Visual Science*, 2008: 49(4):1386-1391). The relative humidity and temperature of ICES systems were monitored daily.

Mice in different groups were labelled using ear marks. The mice were housed in cages (maximum of five animals per cage) and two independent cages were placed in each ICES system. Two schedules were used for topical administration of test compounds, Betaine (0.234% (10 mM) in sterile PBS) or Carnitine (0.25% (10 mM) in sterile PBS), or sterile PBS as another control. Mice without any topical treatment were used as another control. In the first schedule, compounds were administered to mice at the beginning of their housing in ICES (Schedule 1) to study the effect of these compounds on the development of dry eye. In the second schedule compound administration began after mice had been housed in ICES for 21 days (Schedule 2), by which time the dry eye condition had been developed (Chen et al. IOVS 2008), to study the effect of these compounds on treatment of dry eye. Compounds were administered topically to both eyes of the animal. The compound solution made in PBS was topically administered four times daily for up to a total of 35 days for Schedule 1, or 14 days for Schedule 2, during which the mice remained housed in ICES.

Four (4×) mice in each cage received individual treatment: A, B, C, D where

A=Betaine (10 mM in PBS);

B=Carnitine (10 mM in PBS);

C=PBS only;

D=No treatment.

Clinical examination with corneal fluorescein staining was performed on all the eyes on Day 0, 14, 21 and 35 by instilling 0.5 µl of 5% fluorescein solution (1 mg fluorescein sodium in 0.5 ml of PBS) into the inferior conjunctival sac using a micropipette. The cornea was examined using slit-lamp microscopy with cobalt blue light immediately after fluorescein instillation. The stained area was assessed and graded using the 2007 Dry Eye Work Shop (DEW) recommended grading system. The mouse corneas were rated ranging from 0 to 4 with the cornea surface divided into five regions (0 dot, Grade 0; 1-5 dots, Grade 1; 6-15 dots, Grade 2; 16-30 dots, Grade 3; and 30 dots, Grade 4). The total score from the five regions was recorded.

For Schedule 1, six (6×) mice per each group at the end of Day 21 and five (5×) mice from each group at the end of Day 35 post-housing in ICES and undergoing the treatment were sacrificed with an overdose of a mixture of ketamine and xylazine for qRT-PCR evaluation of corneal inflammatory responses. On the other hand, for Schedule 2, three (3×) mice were sacrificed at the end of Day 21, and all the other mice were sacrificed at the end of Day 35 post-housing in ICES and undergoing the treatment. Additionally, seven healthy animals which were not housed in ICES and received no treatment were euthanized as healthy controls for comparison.

qRT-PCR

For qRT-PCR detection of IL-1β, IL-6, IL-17, TNF-α, and GAPDH, total RNA from conjunctivas (2 eyes/group/schedule) were extracted and pooled from each of the five experimental groups using the RNA isolation kit according to the manufacturer's instructions (PicoPure RNA isolation kit, 40 isolations, Arcturus). cDNA was synthesized from 1-µg of total RNA using random primer and M-MuLV reverse transcriptase. The primer sequences for qRT-PCR detection of these mediators have been designed in preparation for qRT-PCR work (Table 1).

TABLE 1

The primer sequences used for qRT-PCR (Forward primers disclosed as SEQ ID NOS 1-5 and Reverse primers disclosed as SEQ ID NOS 6-10, all respectively, in order of appearance.)

| Gene | Forward primer | Reverse primer |
| --- | --- | --- |
| IL-1β | TGAGCTGAAAGCTCTCCACC | CTGATGTACCAGTTGGGGAA |
| IL-6 | AGATAACAAGAAAGACAAAGCCAGAGTC | GCATTGGAAATTGGGGTAGGAAG |
| IL-17 | CTCAACCGTTCCACGTCACCCT | CCAGCTTTCCCTCCGCATT |
| TNF-α | TCTACTGAACTTCGGGGTGATCG | ACGTGGGCTACAGGCTTGTCA |
| GAPDH | TGTCCGTCGTGGATCTGAC | CCTGCTTCACCACCTTCTTG |

Figure 13:
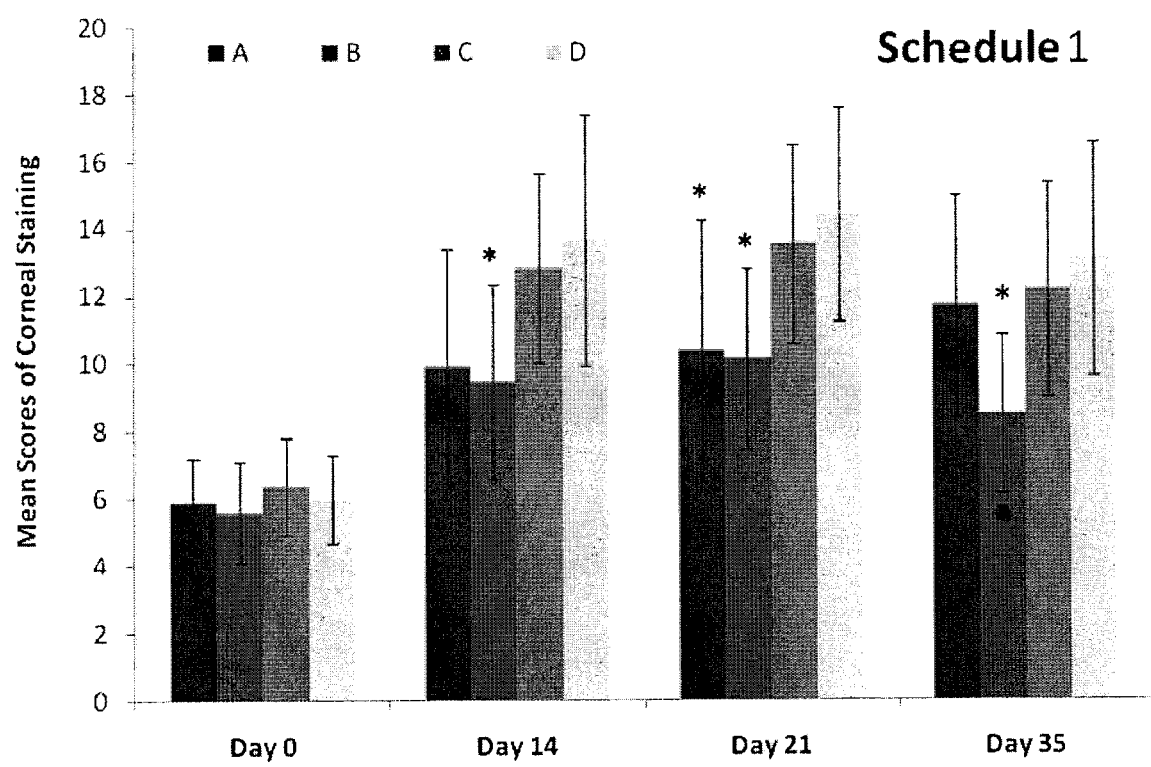
FIG. 13. Mean scores of mouse corneal staining in response to Betaine (10 mM) or Carnitine (10 mM) treatment at the time point of Day 0, 14, 21 or 35 for Schedule 1 where compounds were administered to mice at the beginning of their housing in ICES. Asterisk * shows statistical significant difference compared to the control with PBS (p<0.05) at the same time point.

FIG. 13 shows the mean score of mouse corneal staining on Day 0, 14, 21 or 35 post-housing in ICSE with the topical treatment (A, B, or C) at four times a day starting at the beginning of housing (Schedule 1), or without treatment (D). Both compounds A (Betaine) and B (Carnitine) showed statistically significant reduction in corneal staining on Day 14 and Day 21 as compared to the control C (PBS only) or D (with no treatment), suggesting that the treatment with Betaine or Carnitine slowed down the development of dry eye. However, on Day 35, only compound B (Carnitine) had reduced corneal staining as compared to the control C or D.

Figure 14:
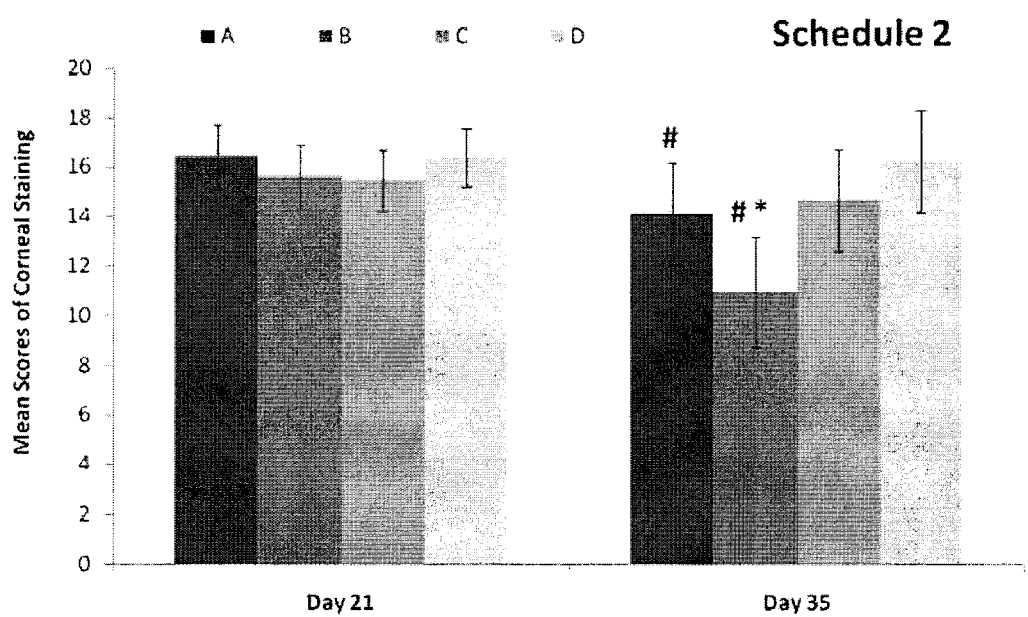
FIG. 14. Comparison of corneal staining scores between four groups at each time point. Asterisk * shows statistical significant difference (P<0.05) comparing B and C treatment groups with the PBS group at Day 35. There were no significant differences between all four groups at the time point of Day 0, Day 14 and Day 21.

After dry eye was developed at Day 21, only the treatment with B (Carnitine) elucidated a statistically significant reduction in the mouse corneal staining as compared to the controls C or D (FIG. 14). However, like Carnitine, Betaine also showed statistically significant reduction in corneal staining from Day 21 to Day 35.

These results suggest Betaine and Carnitine both may have a therapeutic effect in treating dry eye with Carnitine showing a greater effect.

Taken together, both Betaine and Carnitine demonstrated the ability to impede the development of corneal staining, an indication of dry eye. Once the dry eye condition is developed, Carnitine can also reduce the symptoms of dry eye.

Expression of IL-1β, IL-6, IL-17, or TNF-α detected at mRNA level from Real-time PCR were normalized to that of the housekeeping gene GAPDH. Total RNA were collected from the pooled conjunctiva from 2 eyes of each group (total 6× eyes per each treatment group were used for qRT-PCR).

Figures 15A, 15B, 15C, 15D:
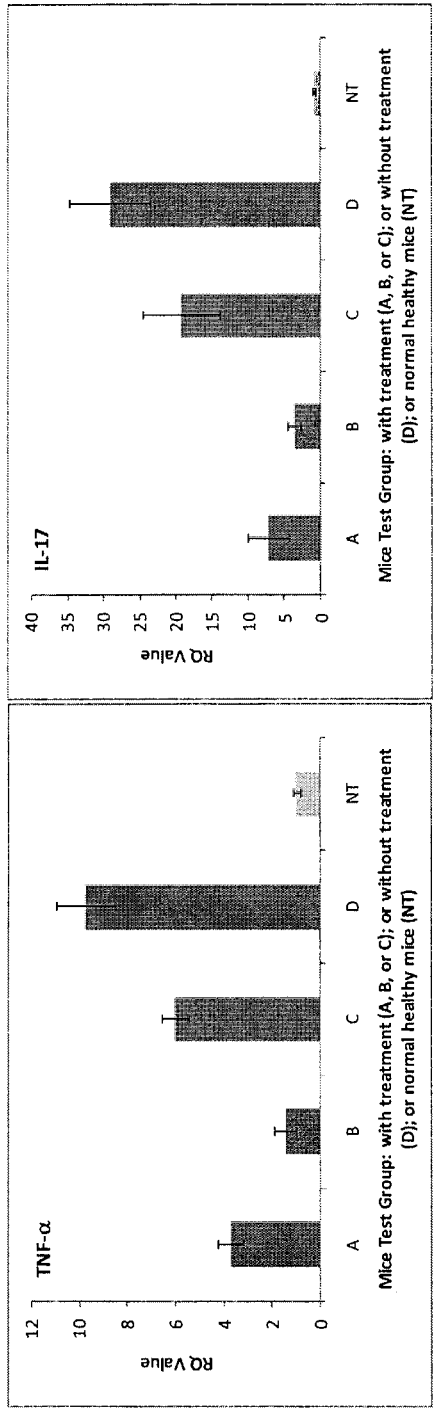
FIGS. 15A, 15B, 15C, and 15D. mRNA expression of TNF-α, IL-17, IL-6 or IL-1β of mice conjunctivas by qRT-PCR after mice were housed in ICSE for 21 days with the topical treatment (A, B, or C) at four times a day starting at the beginning of housing (Schedule 1), or without treatment (D). Normal healthy mice without housing or the treatments were used as normal healthy control.

For Schedule 1 Day 21, the mRNA expression level for each inflammatory mediator was significantly higher in the E group, which was housed in ICSE but received no treatment, than those in the normal healthy (NT) group. The treatment with compound A or B both appeared to result in a statistically significant reduction in expression of all the inflammatory mediators compared to the PBS treatment group, C. Amongst all the compounds, B appeared to have the lowest expression level of TNF-α, IL-17, IL-6 and IL-1β (FIG. 15).

For Schedule 2 Day 35, a statistically significant reduction in expression of TNF-α was found with the treatment with A or as compared to the PBS control (C). However, a statistically significant reduction in IL-17, IL-6 or IL-1β was only found with the treatment group, B (FIG. 16).

Desiccating stress induces secretion of inflammatory cytokines especially IL-1, TNF-α and IL-6 by ocular surface tissues which facilitate activation and migration of resident antigen presenting cells (APC) toward the regional draining lymph nodes. These cytokines are also known as the inducer for Th17 cells, known as IL-17 producing cells. In addition, IL-17 has been evidenced to be associated with disruption of corneal epithelial barrier function, which is the most sight threatening complication of dry eye disease. It induced secretion of MMP-3 and -9 by epithelial cells causing a significant increase in corneal epithelial permeability.

Topical administration of Betaine or Carnitine was observed to delay dry eye development. Both can also lead to diminished dry eye severity suggesting a potential therapeutic effect in treating dry eye. On comparison with Betaine, Carnitine appears to have a greater effect.

Osmotic stress resulting from increased extracellular osmolarity is a major challenge to the normal functioning of cells in a variety of tissues including the corneal epithelium. Tear film hyperosmolarity may increase shedding of the cells of the ocular surface, decrease intercellular connections, cause cell membrane disruptions, and induce apoptosis and inflammation responses in the cells.

In healthy cells, molecular crowding from proteins and protein-bound water leaves very little uncomplexed water. Thus, even minor perturbations of exterior hyperosmolarity can cause drastic changes in cell volume. Exposure of cells to a hyperosmotic environment leads to a dramatic osmotic efflux of water, reduction in cell volume, cell shrinkage, and a concomitant increase in the concentration of all intracellular constituents and elevated ionic strength. The biochemical disequilibrium leads to an irreversible apoptotic cascade and cell death in the event homeostasis is not restored.

As a survival mechanism, resulting decreased cell volume can also signal an osmoregulatory response. Under hypertonic conditions, mechanisms to accumulate compatible osmolytes in cells are stimulated, allowing cells to take up and retain sufficient osmolytes to protect cellular activity under isotonic conditions. Compatible osmolyte accumulation protects cells from ongoing hypertonic insult arising from dry eye syndrome and/or other conditions/diseases. In the current study, HCLE cells exposed to the hyperosmotic conditions in the presence of betaine resulted in a diminished population of shrunken cells compared to those cells under hypertonic shock not in the presence of betaine, suggesting that this compatible organic osmolyte accumulates in HCLE cells to maintain cell volume.

Protection of HCLE by betaine under hyperosmotic stress improved cellular metabolism and survival over the study period of 16 h following application of betaine to 500 mOsm medium. Our experimental evidence further demonstrates that hypertonicity-induced cell shrinkage, if uncompensated by regulatory volume mechanisms, can lead to apoptosis. HCLE cells following exposure to hypertonic conditions exhibited characteristic features of apoptosis including cell shrinkage and rearrangement of phosphatidylserine moieties leading to annexin binding. Further, initiation of necrosis was also shown by PI staining, suggesting an irreversible cascade to cell death if volume is not restored in a timely manner.

Caspase activation is a crucial early event in apoptosis. The activation of caspases is triggered either through the intrinsic (mitochondrial) or extrinsic (death receptor) apoptotic pathways. The intrinsic apoptotic pathway results from alteration in mitochondrial structure and function, releasing cytochrome c from mitochondria and leading to activation of caspases-9. This is followed by activation of downstream caspases, inducing caspase-3/7, resulting in cleavage of several death substrates and subsequent DNA condensation and fragmentation. Initiation of the extrinsic apoptotic pathway resulting from activation of death-domain receptors is followed by activation of caspase-8 which can then activate downstream effector caspase-3/7 independent of mitochondria. Under hyperosmolar conditions, we observed a significant increase in activity of each of the caspases monitored (9, 8 and 3/7), as well as a significant elevation in TNF-α production compared to the isosmotic control. The increase in caspase-8 activity indicates the involvement of the extrinsic pathway accompanied by increased expression of TNF-α, suggesting that HCLE under hypertonic conditions initiated production of this death ligand and activated a self-destruct sequence, triggering the apoptotic cell death. TNF-α triggers apoptosis by binding to the TNF-α receptor which then activates caspase-8. Additionally, the observed increase in caspase-9 activity suggests further TNF-α-independent mechanisms mediating hypertonicity-induced apoptotic cell death via the intrinsic pathway, leading to mitochondrial dysfunction that proceeds apoptosis. Release of cytochrome c from mitochondria and activation of caspase-3 have also been reported in response to hyperosmolarity. Thus both intrinsic and extrinsic apoptotic pathways appear to be stimulated in HCLE in the presence of prolonged exposure to hyperosmotic stress.

TNF-α is involved in reactions relating to inflammatory responses leading to cell-apoptosis and is known to induce activation of MAPK cascades which can lead to pro-apoptotic conditions. Like all death domains, TNF-α may also be involved in death signaling. However, it is important to note that TNF-α induced cell death may play a minor role as compared to its inflammatory responses. Inflammatory responses initiated by TNF-α occur via the components of the NF-κB pathway while those relating to TNF-α induced death occur via recruitment of the Caspase 8.

Addition of betaine to hypertonic medium significantly reduced caspase activity to approach that of the isosmotic controls. The decrease in caspase-9 activity observed in the presence of betaine might partly be due to the reduction in cytochrome c release as a result of cross-talk by caspase-8 activation. Caspase 3/7 activities were decreased as a result of reduction of both caspase-8 and caspase-9, consistent with restoration of mitochondrial activities and cell numbers and volume observed in the betaine-treated group. Our findings show that there is a significant decrease in the expression of Caspase 9 and Caspase 3/7 on addition of L-Carnitine, suggesting that L-Carnitine may inhibit apoptosis via inhibition of the intrinsic pathway. Further observed was marked up-regulation in the expression of TNF-α post hypertonic treatment, yet a very minor difference in expression of Caspase 8 was seen, suggesting that HCLE under osmotic stress may not have initiated cell death via the extrinsic pathway. Instead, increase in the TNF-α alone can suggest activation of inflammatory reactions. These inflammatory responses may be initiated via the NF-κB pathway In summary, exogenous betaine and carnitine stabilize corneal epithelial cell volume under hyperosmotic stress and limit initiation of hyperosmotic stress-induced HCLE apoptosis.

Example 6

This example shows cellular protection by L-carnitine from desiccation and hyperosmolarity.

A in vitro human corneal epithelial cell culture model was used where cells were cultured under a slow drying condition with the culture medium slowly evaporated over the time period of 4-4.5 hours at 34° C. (the temperature of human eyes) to mimic tear film evaporation. The medium osmolarity increased as expected as the culture medium evaporated, whereas the osmolarity of the medium did not change without evaporation.

Figure 17:
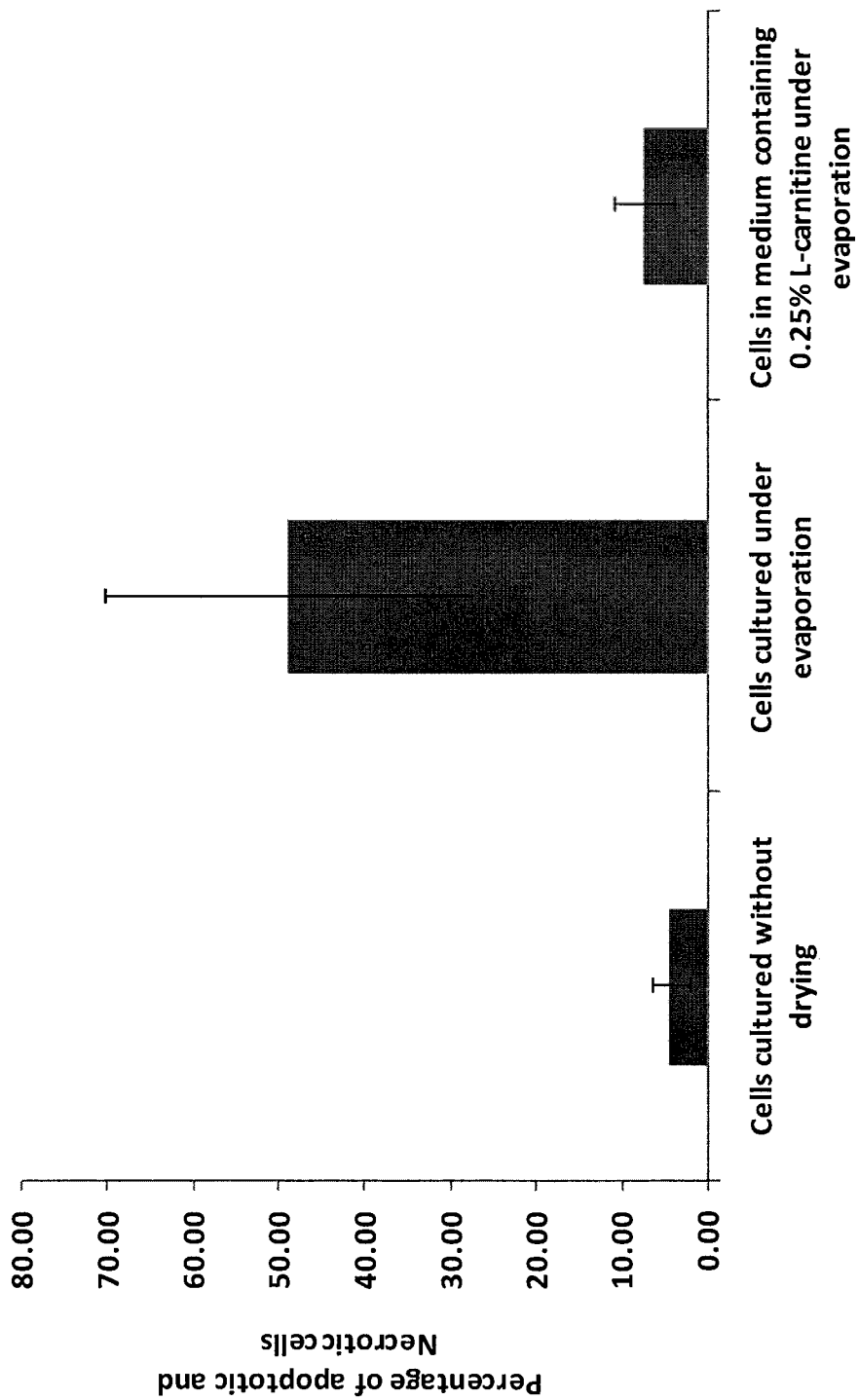
FIG. 17. Percentage of apoptotic/necrotic cells (positive staining to Annexin V/positive staining to Propidium Iodide) in response to the treatment of L-carnitine (0.25% in culture medium) after 4 hrs evaporative drying. The culture medium under normal culture condition without evaporation, or under evaporative drying with no L-carnitine treatment, was used as a control.

The percentage of apoptotic and necrotic cells was low when cells were cultured in the absence of evaporation (FIG. 17, left hand column). The increased osmolarity due to evaporation resulted in cellular damage (apoptotic and necrotic death) as shown in the centre column in FIG. 17. However, the addition of L-carnitine to the culture medium prior to evaporation minimised the cellular damage caused by the increased osmolarity of the culture medium (FIG. 17, right hand column) to a level comparable to the control without evaporation (left hand column).

The invention claimed is:

1. A method for inhibiting, reducing or ameliorating ocular discomfort associated with high tear film tonicity in a subject comprising:
applying an ophthalmic device comprising:
a mixture of osmolytic agents, comprising:
between 5 and 20 mM of one or more carnitine compounds and between 5 and 20 mM of one or more betaine compounds; and
a diffusion attenuator;
wherein the ophthalmic device permits the mixture of osmolytic agents to be desorbed from the ophthalmic device into the eye during wear.

2. A method according to claim 1, wherein the method includes a step of determining whether a subject has or is at risk of developing tear film with high tonicity prior to applying the ophthalmic device.

3. A method according to claim 1, wherein the subject has Dry Eye Syndrome.

4. A method according to claim 1, wherein the betaine compound has a molecular weight of about 600 Da or less.

5. A method according to claim 1, wherein the betaine compound has a molecular weight of about 250 Da less.

6. A method according to claim 1, wherein the betaine compound is selected from the group consisting of trimethylglycine, proline betaine, betaine hydrochloride, beta-alanine betaine, hydroxyproline betaine, cocamidopropylbetaine, carbethoxymethyltrimethylammonium hydroxide and analogs thereof.

7. A method according to claim 1, wherein the betaine compound is selected from the group consisting of trimethylglycine, praline betaine, betaine hydrochloride, beta-alanine betaine and hydroxyproline betaine.

8. A method according to claim 1, wherein the carnitine compound is selected from the group consisting of L-carnitine, alkanoyl L-carnitines including those selected from the group consisting of acetyl, propionyl, isovaleryl, butyryl, and isobutyryl L-carnitine and their pharmaceutically acceptable salts.

9. A method according to claim 1, wherein the carntine compound is L-carnitine.

10. A method according to claim 1, wherein the ophthalmic device is a single use contact lens.

11. A method according to claim 1, wherein the ophthalmic device permits a therapeutically effective amount of the osmolytic agent to be desorbed over about a 12 hour period.

12. A method according to claim 1, wherein the diffusion attenuator is vitamin E.

13. A method according to claim 1, wherein the concentration of the one or more betaine compounds present in the ophthalmic device is 20 mM.

14. A method according to claim 13, wherein the betaine compound is selected from the group consisting of trimethylglycine, proline betaine, betaine hydrochloride, beta-alanine betaine, hydroxyproline betaine, cocamidopropylbetaine, carbethoxymethyltrimethylammonium hydroxide and analogs thereof.

15. A method according to claim 14, wherein the betaine compound is selected from the group consisting of trimethylglycine, praline betaine, betaine hydrochloride, beta-alanine betaine and hydroxyproline betaine.

16. A method according to claim 15, wherein the concentration of the one or more betaine compounds present in the contact lens is 10 mM.

17. A method according to claim 1, wherein the concentration of the one or more carnitine compounds present in the ophthalmic device is 20 mM.

18. A method according to claim 17, wherein the carnitine compound is selected from the group consisting of L-carnitine, alkanoyl L-carnitines including those selected from the group consisting of acetyl, propionyl, isovaleryl, butyryl, and isobutyryl L-carnitine and their pharmaceutically acceptable salts.

19. A method according to claim 18, wherein the carntine compound is L-carnitine.

20. A method according to claim 19, wherein the concentration of the one or more carnitine compounds present in the ophthalmic device is 10 mM.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgagctgaaa gctctccacc                                              20

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agataacaag aaagacaaag ccagagtc                                     28

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctcaaccgtt ccacgtcacc ct                                           22
```

```
<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tctactgaac ttcggggtga tcg                                              23

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgtccgtcgt ggatctgac                                                   19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctgatgtacc agttggggaa                                                  20

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcattggaaa ttggggtagg aag                                              23

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccagctttcc ctccgcatt                                                   19

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acgtgggcta caggcttgtc a                                                21
```

```
-continued

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cctgcttcac caccttcttg                                               20
```